United States Patent [19]

Mandeville, III et al.

[11] Patent Number: 5,624,963

[45] Date of Patent: Apr. 29, 1997

[54] PROCESS FOR REMOVING BILE SALTS FROM A PATIENT AND COMPOSITIONS THEREFOR

[75] Inventors: W. Harry Mandeville, III, Lynnfield; Stephen R. Holmes-Farley, Arlington, both of Mass.

[73] Assignee: GelTex Pharmaceuticals, Inc., Waltham, Mass.

[21] Appl. No.: 258,477

[22] Filed: Jun. 10, 1994

Related U.S. Application Data

[63] Continuation-in-part of Ser. No. 71,564, Jun. 2, 1993, abandoned.

[51] Int. Cl.⁶ .................... B01D 15/00; B01J 39/00
[52] U.S. Cl. .................. 514/789; 210/660; 210/661; 210/903
[58] Field of Search .................. 514/789; 210/660, 210/661, 903

[56] References Cited

U.S. PATENT DOCUMENTS

| | | | |
|---|---|---|---|
| 3,308,020 | 3/1967 | Wolf et al. | 167/65 |
| 3,383,281 | 5/1968 | Wolf et al. | 167/65 |
| 3,787,474 | 1/1974 | Daniels et al. | 260/459 |
| 3,803,237 | 4/1974 | Lednicer et al. | 260/584 R |
| 3,923,972 | 12/1975 | Fields et al. | 424/78 |
| 3,953,406 | 4/1976 | Marsh, Jr. | 260/77.5 |
| 3,980,770 | 9/1976 | Ingelman et al. | 424/79 |
| 4,027,009 | 5/1977 | Grier et al. | 424/78 |
| 4,071,478 | 1/1978 | Shen et al. | 260/2 |
| 4,098,726 | 7/1978 | Wagner et al. | 528/403 |
| 4,101,461 | 7/1978 | Strop et al. | 521/32 |
| 4,111,859 | 9/1978 | Strop et al. | 521/33 |
| 4,198,396 | 4/1980 | Seidel et al. | 424/81 |
| 4,205,064 | 5/1980 | Wagner et al. | 424/78 |
| 4,217,429 | 8/1980 | Wagner et al. | 525/411 |
| 4,340,585 | 7/1982 | Borzatta et al. | 424/79 |
| 4,412,011 | 10/1983 | Kihara et al. | 521/38 |
| 4,540,760 | 9/1985 | Harada et al. | 526/211 |
| 4,557,930 | 12/1985 | Kihara et al. | 424/79 |
| 4,559,391 | 12/1985 | Ueda et al. | 525/366 |
| 4,605,701 | 8/1986 | Harada et al. | 525/107 |
| 4,680,360 | 7/1987 | Ueda et al. | 526/310 |
| 4,759,923 | 7/1988 | Buntin et al. | 424/440 |
| 4,777,042 | 10/1988 | Toda et al. | 424/79 |
| 4,837,015 | 6/1989 | Olsen | 424/79 |
| 5,055,197 | 10/1991 | Albright et al. | 210/638 |
| 5,114,709 | 5/1992 | St. Pierre et al. | 424/78.12 |
| 5,236,701 | 8/1993 | St. Pierre et al. | 424/78.12 |
| 5,374,422 | 12/1994 | St. Pierre et al. | 424/78.12 |
| 5,430,110 | 7/1995 | Ahlers et al. | 525/328.2 |
| 5,451,397 | 9/1995 | Albright et al. | 424/78.01 |

FOREIGN PATENT DOCUMENTS

| | | |
|---|---|---|
| 0081291A3 | 6/1983 | European Pat. Off. . |
| 0162388 | 11/1985 | European Pat. Off. . |
| 0373852A2 | 6/1990 | European Pat. Off. . |
| 0432995A1 | 6/1991 | European Pat. Off. . |
| 0459632A1 | 12/1991 | European Pat. Off. . |
| 0489423A1 | 6/1992 | European Pat. Off. . |
| 0606742A1 | 7/1994 | European Pat. Off. . |
| 0622078A1 | 11/1994 | European Pat. Off. . |
| 929391 | 6/1963 | United Kingdom . |
| 1567294 | 5/1980 | United Kingdom . |
| WO83/02392 | 7/1983 | WIPO . |
| WO91/18027 | 11/1991 | WIPO . |
| WO92/10522 | 6/1992 | WIPO . |
| WO93/05084 | 3/1993 | WIPO . |
| WO93/25595 | 12/1993 | WIPO . |
| WO94/04596 | 3/1994 | WIPO . |
| WO94/27620 | 12/1994 | WIPO . |

OTHER PUBLICATIONS

H. Toda, et al., "Bile Acid Binding and Hypocholesterolemic Activity of a New Anion Exchange Resin from 2–Methylimidazol and Epichlorohydrin," *J. Pharm. Sci.*, 77:531–33 (1988).

A. E. Heming and Thomas L. Flanagan, "Considerations in the Selection of Cation Exchange Resins for Therapeutic Use," *Annals of The New York Academy of Sciences*, 57;239–251 (1954).

N. S. Mason, et al., "A New Ion Exchanger with High in vivo Sodium Capacity," *Kidney International*, 28(17):S–178–S–182 (1985).

*Primary Examiner*—Nathan M. Nutter
*Attorney, Agent, or Firm*—Hamilton, Brook, Smith & Reynolds, P.C.

[57] ABSTRACT

A method for removing bile salts from a patient by ion exchange by administering to the patient a therapeutically effective amount of one or more highly crosslinked polymers characterized by a repeat unit having the formula

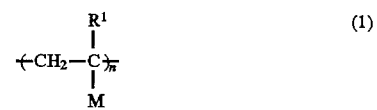

or copolymer thereof, where n is an integer; $R^1$ is H or a $C_1$–$C_8$ alkyl group; M is

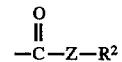

or $-Z-R^2$; Z is O, $NR^3$, S, or $(CH_2)_m$; m=0–10; $R^3$ is H or a $C_1$–$C_8$ alkyl group; and $R^2$ is

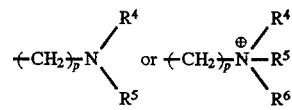

where p=0–10, and each $R^4$, $R^5$, and $R^6$, independently, is H, a $C_1$–$C_8$ alkyl group, or an aryl group, the polymers being non-toxic and stable once ingested.

74 Claims, No Drawings

PROCESS FOR REMOVING BILE SALTS FROM A PATIENT AND COMPOSITIONS THEREFOR

This application is a continuation-in-part of Mandeville et al., U.S. Ser. No. 08/071,564 filed June 2, 1993 entitled "Process for Removing Bile Salts from a Patient and Compositions Therefor," and now abandoned.

BACKGROUND OF THE INVENTION

This invention relates to removing bile salts from a patient.

Sequestering and removing bile salts (e.g., cholate, glycocholate, glycochenocholate, taurocholate, and deoxycholate salts) in a patient can be used to reduce the patient's cholesterol level. Ion exchange resins which, when ingested, remove bile salts via the digestive tract, have been used for this purpose. Removal of bile salts will cause the body to prepare more bile salts. Because the biological precursor to bile salt is cholesterol, the metabolism of cholesterol to make bile salts is accompanied by a simultaneous reduction in the cholesterol in the patient.

SUMMARY OF THE INVENTION

In a first aspect, the invention features a method of removing bile salts from a patient by ion exchange that includes administering to the patient a therapeutically effective amount of one or more highly crosslinked polymers that are non-toxic and stable once ingested. The polymers are characterized by a repeat unit having the formula

(1)

or copolymer thereof, where n is an integer; $R^1$ is H or a $C_1$–$C_8$ alkyl group (which may be straight chain or branched, substituted or unsubstituted, e.g., methyl); M is

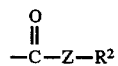

or —Z—$R^2$; Z is O, $NR^3$ S or $(CH_2)_m$; m=0–10; $R^3$ is H or a $C_1$–$C_8$ alkyl group (which may be straight chain or branched, substituted or unsubstituted, e.g., methyl); and $R^2$ is

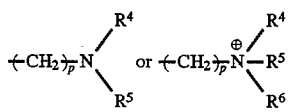

where p=0–10, and each $R^4$, $R^5$, and $R^6$, independently, is H, a C1–$C_8$ alkyl group (which may be straight chain or branched, substituted or unsubstituted, e.g., methyl), or an aryl group (e.g., having one or more rings and which may be substituted or unsubstituted, e.g., phenyl, naphthyl, imidazolyl, or pyridyl).

By "non-toxic" it is meant that when ingested in therapeutically effective amounts neither the polymers nor any ions released into the body upon ion exchange are harmful. Preferably, the ions released into the body are actually beneficial to the patient. Such is the case when, for example, the exchangeable ions are natural nutrients such as amino acids.

By "stable" it is meant that when ingested in therapeutically effective amounts the polymers do not dissolve or otherwise decompose to form potentially harmful by-products, and remain substantially intact so that they can transport ions following ion exchange out of the body.

In preferred embodiments, the polymer is crosslinked by means of a multifunctional crosslinking co-monomer, the co-monomer being present in an amount from about 1–25% (more preferably about 2.5–20%) by weight, based upon total monomer weight.

The polymer further preferably includes one or more hydrophobic co-monomers, e.g., styrene, vinyl naphthalene, ethyl vinylbenzene, N-alkyl and N-aryl derivatives of acrylamide and methacrylamide, alkyl and aryl acrylates, alkyl and aryl methacrylates, 4-vinylbiphenyl, 4-vinylanisole, 4-aminostyrene, and fluorinated derivatives of any of these co-monomers (e.g., p-fluorostyrene, pentafluorostyrene, hexafluoroisopropylacrylate, hexafluorobutylmethacrylate, or heptadecafluorodecylmethacrylate). The alkyl groups are preferably $C_1$–$C_{15}$ alkyl groups, and may be straight chain, branched, or cyclic (e.g., cyclohexyl), and may further be substituted or unsubstituted. The aryl groups preferably have one or more rings and may be substituted or unsubstituted, e.g., phenyl, naphthyl, imidazolyl, or pyridyl. The polymer may also include one or more positively charged co-monomers, e.g., vinyl pyridine, dimethylaminomethyl styrene, or vinyl imidazole.

One example of a preferred polymer is characterized by a repeat unit having the formula

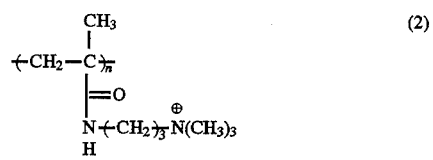
(2)

or copolymer thereof. The polymer may further include, as a co-monomer, one or more of the following: n-butylmethacrylamide, hexafluorobutylmethacrylate, heptadecafluorodecylmethacrylate, styrene or fluorinated derivatives thereof, 2-vinyl naphthalene, 4-vinyl imidazole, vinyl pyridine, trimethylammoniumethylmethacrylate, trimethylammoniumethylacrylate, 4-vinylbiphenyl, 4-vinylanisole, or 4-aminostyrene.

A second example of a preferred polymer is characterized by a repeat unit having the formula

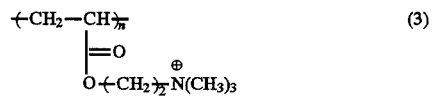
(3)

or copolymer thereof. The polymer may also include, as a co-monomer, one or more of the following: isopropylacrylamide, styrene or fluorinated derivatives thereof, hexafluoroisopropylacrylate, and trimethylammoniumethylmethacrylate.

A third example of a preferred polymer is characterized by a repeat unit having the formula

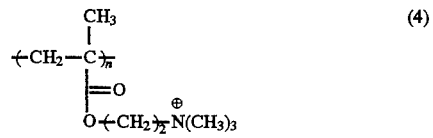
(4)

or copolymer thereof. The polymer may also include, as a co-monomer, styrene or a fluorinated derivative thereof.

A fourth example of a preferred polymer is characterized by a repeat unit having the formula

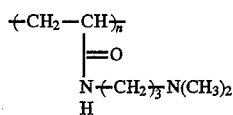

(5)

or copolymer thereof.

A fifth example of a preferred polymer is characterized by a repeat unit having the formula

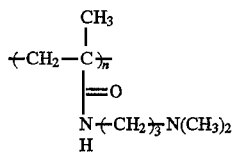

(6)

or copolymer thereof.

A sixth example of a preferred polymer is characterized by a repeat unit having the formula

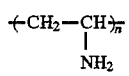

(7)

or copolymer thereof. The polymer may further include, as a co-monomer, ethyl vinylbenzene.

A seventh example of a preferred polymer is characterized by a repeat unit having the formula

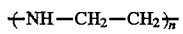

(8)

or copolymer thereof.

An eighth example of a preferred polymer is characterized by a repeat unit having the formula

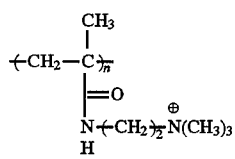

(11)

or copolymer thereof. The polymer may also include, as a co-monomer, styrene or a fluorinated derivative thereof.

In a second aspect, the invention features a method for removing bile salts from a patient by ion exchange that includes administering to the patient a therapeutically effective amount of one or more highly crosslinked polymers characterized by a repeat unit having the formula

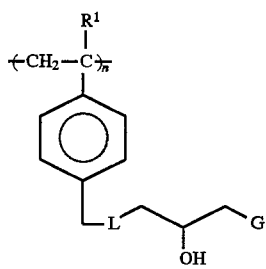

(12)

or copolymer thereof, where n is an integer; $R^1$ is H or a $C_1$-$C_8$ alkyl group; L is —NH— or G is

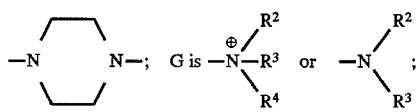

and each $R^2$, $R^3$, and $R^4$, independently, is H, a $C_1$-$C_8$ alkyl group, or an aryl group. The polymers are non-toxic and stable once ingested.

In preferred embodiments, the polymer is crosslinked by means of a multifunctional crosslinking co-monomer which is present in an amount from about 1–25% by weight (and preferably from about 2.5–20% by weight), based upon total monomer weight. The polymer further preferably includes one or more of the above-described hydrophobic co-monomers One example of a preferred polymer is characterized by a repeat unit having the formula

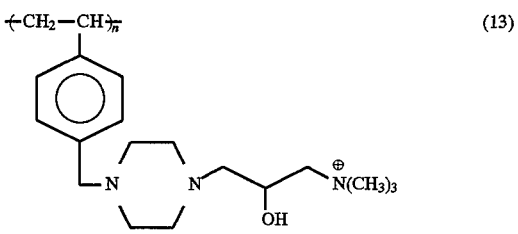

(13)

or copolymer thereof. The polymer may further include, as a co-monomer, styrene or a fluorinated derivative thereof.

A second example of a preferred polymer is characterized by a repeat unit having the formula

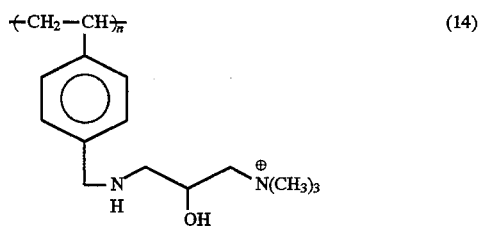

(14)

or copolymer thereof.

The polymers according to the first and second aspects of the invention may have fixed positive charges, or may have the capability of becoming charged upon ingestion at physiological pH. In the latter case, the charged ions also pick up negatively charged counterions upon ingestion that can be exchanged with bile salts. In the case of polymers having fixed positive charges, however, the polymer may be provided with one or more exchangeable counterions. Examples of suitable counterions include Cl$^-$, Br$^-$, $CH_3OSO_3^-$, $HSO_4^-$, $SO_4^{2-}$, $HCO_3^-$, $CO_3^-$, acetate lactate succinate, propionate, butyrate, ascorbate, citrate, maleate, folate, an amino acid derivative, a nucleotide, a lipid, or a phospholipid. The counterions may be the same as, or different from, each other. For example, the polymer may contain two different types of counterions, both of which are exchanged for the bile salts being removed. More than one polymer, each having different counterions associated with the fixed charges, may be administered as well.

The invention also features therapeutic compositions for removing bile salts that include a therapeutically effective amount of one or more of the above-described polymers.

In another aspect, the invention features a highly crosslinked polymer composition that includes a polymer characterized by a repeat unit having the formula

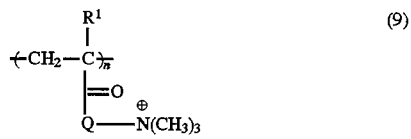

(9)

where $R^1$ is H or methyl, Q is —NH—$(CH_2)_3$— or —O—$(CH_2)_2$ and n is an integer, and at least one additional co-monomer selected from the group consisting essentially of vinylnaphthalene, vinylimidazole, fluorinated derivatives of styrene, and fluorinated alkyl methacrylates.

In some preferred embodiments of this aspect, $R^1$ is methyl and Q is —NH—$(CH_2)_3$—. This polymer may further comprise, as a co-monomer, trimethylammoniumethylacrylate or trimethylammoniumethylmethacrylate. In other preferred embodiments, Q is —O—$(CH_2)_2$.

Examples of suitable fluorinated styrene derivatives include p-fluorostyrene and pentafluorostyrene. Examples of suitable fluorinated alkyl methacrylates include hexafluorobutyl methacrylate and heptadecafluorodecyl methacrylate.

In yet another aspect, the invention features a highly crosslinked polymer composition that includes a polymer characterized by a repeat unit having the formula

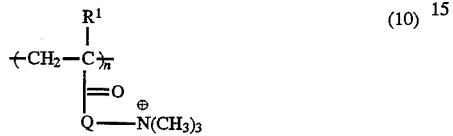

where $R^1$ is H or methyl, Q is —NH—$(CH_2)_3$—or —O—$(CH_2)_2$ and n is an integer, and, as additional co-monomers, (a) styrene and (b) trimethylammoniumethylacrylate or trimethylammoniumethylmethacrylate when $R^1$ is methyl and Q is —NH—$(CH_2)_3$—

In an additional aspect, the invention features a method of synthesizing a highly crosslinked polymer having hydrophilic and hydrophobic units that includes reacting hydrophilic and hydrophobic monomers in the presence of an alcoholic solvent.

In yet another aspect, the invention features a method for removing bile salts from a patient that includes administering to the patient a therapeutically effective amount of the reaction product of:

(a) one or more highly crosslinked polymers characterized by a repeat unit having the formula:

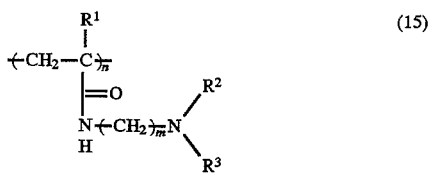

and salts and copolymers thereof, where n and m are integers and each $R^1$, $R^2$, and $R^3$, independently, is H or a $C_1$–$C_8$ alkyl group; and (b) at least one alkylating agent, The reaction product is non-toxic and stable once ingested.

By "salt" it is meant that the amine nitrogen group in the repeat unit is protonated to create a positively charged nitrogen atom associated with a negatively charged counterion.

By "alkylating agent" it is meant a reactant which, when reacted with the crosslinked polymer, causes an alkyl group or derivative thereof (e.g., an aralkyl, hydroxyalkyl, alkylammonium salt, alkylamide, or combination thereof) to be covalently bound to one or more of the nitrogen atoms of the polymer.

In preferred embodiments, the reaction product is crosslinked by means of a multifunctional crosslinking co-monomer, the co-monomer being present in an amount from about 1–25% (more preferably about 2.5–20%) by weight, based upon total weight monomer weight.

One example of a preferred polymer is characterized by a repeat unit having the formula

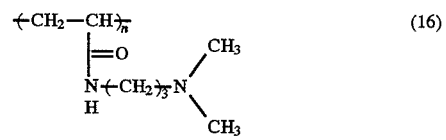

or a salt or copolymer thereof.

A second example of a preferred polymer is characterized by a repeat unit having the formula

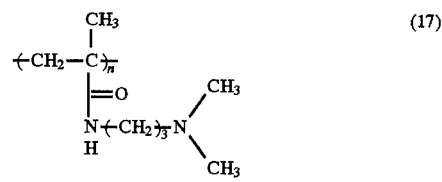

or a salt or copolymer thereof.

Preferred alkylating agents have the formula RX where R is a $C_1$–$C_{20}$ alkyl, $C_1$–$C_{20}$ hydroxyalkyl, $C_1$–$C_{20}$ aralkyl, $C_1$–$C_{20}$ alkylammonium, or $C_1$–$C_{20}$ alkylamido group and X includes one or more electrophilic leaving groups. By "electrophilic leaving group" it is meant a group which is displaced by a nitrogen atom in the crosslinked polymer during the alkylation reaction. Examples of preferred leaving groups include halide, epoxy, tosylate, and mesylate group. In the case of, e.g., epoxy groups, the alkylation reaction causes opening of the three-membered epoxy ring.

Examples of preferred alkylating agents include a $C_1$–$C_{20}$ alkyl halide (e.g., an n-butyl halide, n-hexyl halide, n-octyl halide, n-decyl halide, n-dodecyl halide, n-tetradecyl halide, n-octadecyl halide, and combinations thereof); a $C_1$–$C_{20}$ dihaloalkane (e.g., a 1,10-dihalodecane); a $C_1$–$C_{20}$ hydroxyalkyl halide (e.g., an 11-halo-1-undecanol); a $C_1$–$C_{20}$ aralkyl halide (e.g., a benzyl halide); a $C_1$–$C_{20}$ alkyl halide ammonium salt (e.g., a (4-halobutyl) trimethylammonium salt, (6-halohexyl) trimethylammonium salt, (8-halooctyl) trimethylammonium salt, (10-halodecyl) trimethylammonium salt, (12-halododecyl) trimethylammonium salts and combinations thereof); a $C_1$–$C_{20}$ alkyl epoxy ammonium salt (e.g., a (glycidylpropyl)trimethylammonium salt); and a $C_1$–$C_{20}$ epoxy alkylamide (e.g., an N-(2,3-epoxypropane) butyramide, N-(2,3-epoxypropane) hexanamide, and combinations thereof).

It is particularly preferred to react the polymer with at least two alkylating agents. In one preferred example, one of the alkylating agents has the formula RX where R is a $C_1$–$C_{20}$ alkyl group and X includes one or more electrophilic leaving groups (e.g., an alkyl halide), and the other alkylating agent has the formula R'X where R' is a $C_1$–$C_{20}$ alkyl ammonium group and X includes one or more electrophilic leaving groups (e.g., an alkyl halide ammonium salt).

In another preferred example, one of the alkylating agents has the formula RX where R is a $C_1$–$C_{20}$ alkyl group and X includes one or more electrophilic leaving groups (e.g., an alkyl halide), and the other alkylating agent has the formula R'X where R' is a $C_1$–$C_{20}$ hydroxyalkyl group and X includes one or more electrophilic leaving groups (e.g., a hydroxy alkyl halide).

In another preferred example, one of the alkylating agents is a $C_1$–$C_{20}$ dihaloalkane and the other alkylating agent is a $C_1$–$C_{20}$ alkylammonium salt.

The invention provides an effective treatment for removing bile salts from a patient (and thereby reducing the patient's cholesterol level). The compositions are nontoxic and stable when ingested in therapeutically effective amounts.

The invention further provides an effective synthesis for polymers having hydrophilic and hydrophobic units by conducting the reaction in the presence of an alcoholic solvent not normally considered a good polymerization solvent due to its chain transfer properties.

Other features and advantages will be apparent from the following description of the preferred embodiments thereof and from the claims.

DESCRIPTION OF THE PREFERRED EMBODIMENTS

Compositions

Preferred polymer have the formulae set forth in the Summary of the Invention, above. The polymers are highly crosslinked. The high level of crosslinking makes the polymers completely insoluble and thus limits the activity of the alkylated reaction product to the gastrointestinal tract only. Thus, the compositions are non-systemic in their activity and will lead to reduced side-effects in the patient.

The polymers are preferably crosslinked by adding a crosslinking co-monomer to the reaction mixture during polymerization. Examples of suitable crosslinking co-monomers include diacrylates and dimethacrylates (e.g., ethylene glycol diacrylate, propylene glycol diacrylate, butylene glycol diacrylate, ethylene glycol dimethacrylate, propylene glycol dimethacrylate, butylene glycol dimethacrylate, polyethyleneglycol dimethacrylate, polyethyleneglycol diacrylate), methylene bisacrylamide, methylene bismethacrylamide, ethylene bisacrylamide, ethylenebismethacrylamide, ethylidene bisacrylamide, divinyl benzene, bisphenol A dimethacrylate, and bisphenol A diacrylate. These crosslinking co-monomers are either commercially available or are prepared as described in Mandeville et al., "Process for Adjusting Ion Concentration in a Patient and Compositions Therefor, " U.S. Ser. No. 08/065,113, filed May 20, 1993, assigned to the same assignee as the present application and hereby incorporated by reference. The amount of crosslinking agent is typically between 1.0 and 25 weight %, based upon combined weight of crosslinking agent and monomer, with 2.5–20% being preferred.

Preferably, the polymer includes one or more co-monomers that increase the overall hydrophobicity of the polymer. Because bile salts are hydrophobic, the hydrophobic co-monomer aids in maximizing the selectivity of the interaction of the polymer with the bile salts.

Examples of suitable hydrophobic co-monomers include, e.g., acrylamide, methacrylamide, and N-alkyl (e.g., methyl, ethyl, isopropyl, butyl, hexyl, dodecyl, cyclohexyl, dicyclohexyl) and N-aryl (e.g., phenyl, diphenyl) derivatives thereof; alkyl and aryl acrylates and methacrylates (e.g., ethyl, propyl, butyl, dodecyl), and fluorinated derivatives thereof (e.g., hexafluoroisopropyl acrylate, hexafluorobutyl methacrylate, heptadecafluorodecyl acrylate); styrene and derivatives thereof (e.g., dimethylaminomethyl styrene, 4-aminostyrene, and fluorinated derivatives, e.g., p-fluorostyrene, pentafluorostyrene); ethylvinylbenzene; vinyl naphthalene; vinyl pyridine; vinyl imidazole; 4-vinylbiphenyl; 4,4-vinylanisole; and combinations thereof. The amount of hydrophobic co-monomer used in the preparation of these polymers is from 1 to 75% by weight, preferably from 3 to 65%.

The level of hydrophobicity needed may also be achieved simply by appropriate choice of crosslinking co-monomer. For example, divinylbenzene is a suitable crosslinking co-monomer and is hydrophobic as well. In addition, the main "impurity" in divinylbenzene is ethylvinylbenzene, a hydrophobic, polymerizable monomer which will also contribute to the overall hydrophobicity of the polymer. Other hydrophobic crosslinking co-monomers include bisphenol A diacrylate and bisphenol A dimethacrylate.

The crosslinked polymers may be reacted with one or more alkylating agents. Examples of preferred alkylating agents are set forth in the Summary of the Invention, above.

EXAMPLES

A. Polymer Preparation

1. Preparation of Poly(methacrylamidopropyltrimethylammonium chloride) (PolyMAPTAC)

To a 1000 mL, three-necked, round-bottomed flask was added the following: methacrylamidopropyltrimethylammonium chloride (MAPTAC) (40 mL of a 50% aqueous solution, 21 g), ethylene glycol dimethacrylate crosslinking co-monomer (5.00 g, 4.76 mL), ethyl acetate (200 mL), and 2-propanol (200 mL). The resulting solution was clear. Next, the polymerization initiator AIBN (0.1 g) was added and the reaction mixture was heated to 65° C. When the temperature reached 65° C. the solution was degassed with nitrogen for 5 minutes, at which point it turned cloudy, indicating that polymerization was proceeding. The reaction was maintained at 65° C. for another 3 hours and then allowed to cool to room temperature.

The resulting polymer (which was hard and sticky) was combined with 500 mL of water to soften it, and then transferred to a blender where it was blended with 1500 mL of 2-propanol and centrifuged. The mixture was then decanted and transferred to another blender with the aid of 100 mL of water. 800 mL of 2-propanol was then added and the mixture was blended, allowed to settle, and decanted. The mixture was then combined with 1000 mL of 2-propanol, blended, filtered, and vacuum-dried to afford 12.6 g of polymer.

PolyMAPTAC crosslinked with 0.5% methylenebismethacrylamide crosslinking co-monomer; polyMAPTAC crosslinked with 10% methylenebismethacrylamide crosslinking co-monomer; and polyMAPTAC crosslinked with 10% divinylbenzene crosslinking co-monomer were prepared in analogous fashion.

2. Preparation of Poly (vinylamine)

The first step involved the preparation of ethylidenebisacetamide. Acetamide (118 g), acetaldehyde (44.06 g), copper acetate (0.2 g), and water (300 mL) were placed in a 1 L three neck flask fitted with condenser, thermometer, and mechanical stirrer. Concentrated HCl(34 mL) was added and the mixture was heated to 45°–50° C. with stirring for 24 h. The water was then removed in vacuo to leave a thick sludge which formed crystals on cooling to 5° C. Acetone (200 mL) was added and stirred for a few minutes, after which the solid was filtered off and discarded. The acetone was cooled to 0° C and solid was filtered off. This solid was rinsed in 500 mL acetone and air dried 18 h to yield 31.5 g of ethylidenebisacetamide.

The next step involved the preparation of vinylacetamide from ethylidenebisacetamide. Ethylidenebisacetamide (31.05 g), calcium carbonate (2 g) and celite 541 (2 g) were placed in a 500 mL three neck flask fitted with a thermometer, a mechanical stirrer, and a distilling head atop a Vigreux column. The mixture was vacuum distilled at 35 mm Hg by heating the pot to 180°–225° C. Only a single fraction was collected (10.8 g) which contained a large portion of acetamide in addition to the product (determined by NMR). This solid product was dissolved in isopropanol (30 mL) to form the crude vinylacetamide solution used for polymerization.

Crude vinylacetamide solution (15 mL), divinylbenzene (1 g, technical grade, 55% pure, mixed isomers), and AIBN (0.3 g) were mixed and heated to reflux under a nitrogen atmosphere for 90 min, forming a solid precipitate. The solution was cooled, isopropanol (50 mL) was added, and the solid was collected by centrifugation. The solid was rinsed twice in isopropanol, once in water, and dried in a vacuum oven to yield 0.8 g of poly(vinylacetamide), which was used to prepare poly(vinylamine as follows).

Poly(vinylacetamide) (0.79 g) was placed in a 100 mL one neck flask containing water (25 mL) and conc. HCl (25 mL). The mixture was refluxed for 5 days, after which the solid was filtered off, rinsed once in water, twice in isopropanol, and dried in a vacuum oven to yield 0.77 g of product. Infrared spectroscopy indicated that a significant amount of the amide (1656 cm$^{-1}$) remained and that not much amine (1606 cm$^{-1}$) was formed. The product of this reaction (~0.84 g) was suspended in NaOH (46 g) and water (46 g) and heated to boiling (~140°0 C.). Due to foaming the temperature was reduced and maintained at ~100° C for 2 h. Water (100 mL) was added and the solid collected by filtration. After rinsing once in water the solid was suspended in water (500 mL) and adjusted to pH 5 with acetic acid. The solid was again filtered off, rinsed with water, then isopropanol, and dried in a vacuum oven to yield 0.51 g of product. Infrared spectroscopy indicated that significant amine had been formed.

3. Preparation of Poly(3-dimethylaminopropylacrylamide (DMAPA)

Dimethylaminopropylacrylamide (10 g) and methylenebisacrylamide crosslinking co-monomer (1.1 g) were dissolved in 50 mL of water in a 100 mL three neck flask. The solution was stirred under nitrogen for 10 minutes. Potassium persulfate (0.3 g) and sodium metabisulfite (0.3 g) were each dissolved in 2–3 mL of water and then mixed. After a few seconds this solution was added to the monomer solution, still under nitrogen. A gel formed immediately and was allowed to sit overnight. The gel was removed and blended with 500 mL of isopropanol. The solid was filtered off and rinsed three times with acetone. The solid white powder was filtered off and dried in a vacuum oven to yield 6.1 g.

4. Preparation of Poly(dimethylaminopropylacrylamide hydrochloride) (DMAPA. HCl)

Dimethylaminopropylacrylamide (20.10 g) was dissolved in water (100 mL) and neutralized with concentrated HCl to pH 6.95. Methylenebisacrylamide crosslinking co-monomer (2.2 g) and water (100 mL) were added and warmed (34°0 C.) to dissolve. Potassium persulfate (0.2 g) and potassium metabisulfite (0.2 g) were added with stirring. After gellation, the solution was allowed to sit for 6 h, blended with isopropanol (600 mL) three times, and dried in a vacuum oven to yield 14.47 g of the title polymer.

PolyDMAPA.HCl crosslinked with 10% methylenebismethacrylamide crosslinking co-monomer was prepared in analogous fashion.

5. Preparation of Poly (dimethylaminopropylmethacrylamide hydrochloride) (DMAPMA. HCl)

Dimethylaminopropylmethacrylamide (20.0 g) was dissolved in water (100 mL) and neutralized with concentrated HCl to pH 6.94. Methylenebisacrylamide crosslinking co-monomer (2.2 g) was added and the solution was warmed (39° C.) to dissolve. Potassium persulfate (0.3 g) and potassium metabisulfite (0.3 g) were added with stirring under a nitrogen atmosphere. After gellation, the solution was allowed to sit overnight, blended with isopropanol (500 mL) twice, and dried in a vacuum oven to yield 27.65 g of product. Some of the solid (3.2 g; sieved to −80/+200 mesh size) was stirred in water (100 mL) for 50 min, additional water (100 mL) was added and the solution stirred for 36 min. The solid was collected by centrifugation, resuspended in water (400 mL), stirred 150 min, and again collected by centrifugation. The solid was finally resuspended in water (500 mL), stirred 90 min, and collected by filtration. The solid was dried in a vacuum oven to yield 0.28 g of the title polymer.

6. Preparation of Poly (methacrylamidopropyltrimethylammonium chloride) co-poly(n-butylmethacrylamide) (MAPTAC co-BuMA)

The co-monomer n-butylmethacrylamide (BuMA) was prepared as follows.

Methacryloyl chloride (48.4 mL, 52.3 g, 0.500 mol) was dissolved in tetrahydrofuran (300 mL) in a 1 L flask and placed in an ice bath. A solution containing butylamine (36.6 g) and triethylamine (55.6 g) was added dropwise, maintaining the temperature at 5°–15° C. After addition the solution was stirred for 5 min and the solid triethylamine hydrochloride was filtered off and discarded. The solvent was removed in vacuo from the mother liquor and the resulting yellow oil was used without further purification. The yield was 71.58 g of BuMA co-monomer.

To a 1000 mL, three-necked, round-bottomed flask was added the following: methacrylamidopropyltrimethylammonium chloride (MAPTAC) (108 mL of a 50% aqueous solution, 56.8 g), ethylene glycol dimethacrylate crosslinking co-monomer (19.62 g), BuMA co-monomer (12.12 g), and 2-propanol (850 mL). The resulting solution was clear. Next, the reaction mixture was heated to 40° C. while being degassed with nitrogen. When the solution had reached 40° C., the catalyst, consisting of a solution of potassium persulfate (0.75 g) and potassium metabisulfate (0.75 g) in 25 mL of water was added. The solution immediately began to turn cloudy, indicating that polymerization was proceeding. The reaction was maintained at 40° C. for 24 hours and then allowed to cool to room temperature.

The resulting polymer was filtered and washed on the funnel with isopropanol and vacuum dried to afford 64.54 g of the title polymer.

Polymer for testing was washed two times with 800 mL of water each time, followed by two washes with 500 mL of methanol each time to give 34.5 g of purified polymer.

A crosslinked MAPTAC co-BuMA copolymer was also prepared using propylene glycol dimethacrylate, rather than ethylene glycol dimethacrylate, as the crosslinking co-monomer, as follows.

To a 1000 mL, three-necked, round-bottomed flask was added the following: methacrylamidopropyltrimethylammonium chloride (MAPTAC) (60 mL of a 50% aqueous solution, 31.5 g), propylene glycol dimethacrylate crosslinking co-monomer (9.81 g), BuMA co-monomer (6.06 g), and 2-propanol (300 mL). The resulting solution was clear. Next, the reaction mixture was heated to 70° C. while being degassed with nitrogen. When the solution had reached 70° C, the catalyst, AIBN (0.50 g), was added. The solution immediately began to turn cloudy, indicating that polymerization was proceeding. The reaction was maintained at 70° C. for 6 hours and then allowed to cool to room temperature.

The resulting polymer was filtered and washed on the funnel with isopropanol and vacuum dried to afford 23.3 g of polymer.

MAPTAC coBuMA (5%) crosslinked with 24% ethyleneglycoldimethacrylate crosslinking co-monomer, MAP- TAC coBuMA (2)%) crosslinked with 0.5% methylenebismethacrylamide crosslinking co-monomer, and MAPTAC coBuMA (14%) crosslinked with 22% propyleneglycoldimethacrylate crosslinking co-monomer were prepared in analogous fashion by adjusting the ratios of starting monomers.

7. Preparation of Poly(methacrylamidopropyltrimethylammonium chloride) co-poly(styrene) (MAPTAC co-Sty)

To a 1000 mL, three-necked, round-bottomed flask was added the following: methacrylamidopropyltrimethylammonium chloride (MAPTAC) (60 mL of a 50% aqueous solution, 31.5 g), divinyl benzene crosslinking co-monomer (2.00 g), styrene co-monomer (1.75 g), and 2-propanol (300 mL). The resulting solution was clear. Next, the reaction mixture was heated to 60° C. while being degassed with nitrogen. When the solution had reached 60° C., the catalyst, AIBN (0.50 g), was added. The solution immediately began to turn cloudy, indicating that polymerization was proceeding. The reaction was maintained at 60° C. for 24 hours and then allowed to cool to room temperature. After about 7 hours the mixture had become very thick and 100 mL additional isopropanol was added to allow for better stirring.

The resulting polymer was filtered and washed on the funnel with isopropanol and vacuum dried to afford 30.9 g of the title polymer.

Polymer for testing was washed two times with 1000 mL of water each time followed by two washes with 800 mL of methanol each time to give 28.0 g of purified polymer.

MAPTAC co-Sty (13%) crosslinked with 7.5% butyleneglycoldimethacrylate crosslinking co-monomer, MAPTAC co-Sty (13%) crosslinked with 20% butyleneglycoldimethacrylate crosslinking co-monomer, MAPTAC co-Sty (19%) crosslinked with 6% divinylbenzene co-monomer, MAPTAC co-Sty (23%) crosslinked with 7% divinylbenzene co-monomer, MAPTAC co-Sty (30%) crosslinked with 6% divinylbenzene co-monomer, and MAPTAC co-Sty (38%) crosslinked with 6% divinylbenzene co-monomer were prepared in analogous fashion by varying the ratios of starting monomers.

8. Preparation of Poly(methacrylamidopropyltrimethylammonium chloride) co-poly(vinyl naphthalene) (MAPTAC co-VN)

To a 1000 mL, three-necked, round-bottomed flask was added the following: methacrylamidopropyltrimethylammonium chloride (MAPTAC) (40 mL of a 50% aqueous solution, 21.0 g), divinyl benzene crosslinking co-monomer (2.25 g), 2-vinylnaphthalene co-monomer (10.5 g), and 2-propanol (320 mL). The resulting solution was clear. Next, the reaction mixture was heated to 65° C. while being degassed with nitrogen. When the solution had reached 65° C., the catalyst, AIBN (0.50 g), was added. The solution immediately began to turn cloudy, indicating that polymerization was proceeding. The reaction was maintained at 65° C. for 20 hours and then allowed to cool to room temperature.

The resulting polymer was filtered and washed on the funnel with isopropanol and then immediately slurried in 400 mL of distilled water. The mixture was stirred for ½ hour and then filtered. The water wash was repeated one more time. The filter cake was then slurried in 400 mL of methanol and stirred for ½ hour. The mixture was filtered and the methanol slurry was repeated one more time. Vacuum drying afforded 22.11 g, 65.5% of the title polymer.

MAPTAC co-VN (39%) crosslinked with 5% divinyl benzene crosslinking co-monomer was prepared in analogous fashion by varying the ratio of starting monomers.

9. Preparation of Poly(methacrylamidopropyltrimethylammonium chloride) co-poly(1-vinyl imidazole) (MAPTAC co-VI)

To a 1000 mL, three-necked, round-bottomed flask was added the following: methacrylamidopropyltrimethylammonium chloride (MAPTAC) (40 mL of a 50% aqueous solution, 21.0 g), divinyl benzene crosslinking co-monomer (2.25 g), 1-vinylimidazole co-monomer (12.54 g), and 2-propanol (300 mL). The resulting solution was clear. Next, the reaction mixture was heated to 65° C. while being degassed with nitrogen. When the solution had reached 65° C., the catalyst, AIBN (0.50 g), was added. The solution immediately began to turn cloudy, indicating that polymerization was proceeding. The reaction was maintained at 65°0 C. for 20 hours and then allowed to cool to room temperature.

The resulting polymer was filtered and washed on the funnel with isopropanol, and then immediately slurried in 500 mL of distilled water. The mixture was stirred for ½ hour and then filtered. The water wash was repeated one more time. The filter cake was then slurried in 400 mL of methanol and stirred for ½ hour. The mixture was filtered and the methanol slurry was repeated one more time. Vacuum drying afforded 7.34 g, 20.5% of the title polymer.

10. Preparation of Poly(trimethylammoniumethylacrylatechloride) co-poly(styrene) (TMAEAC co-Sty)

To a 1000 mL, three-necked, round-bottomed flask was added the following: trimethylammoniumethylacrylatechloride (TMAEAC) (99.4 mL of a 50% aqueous solution, 53.0 g), divinyl benzene crosslinking co-monomer (7.00 g), styrene co-monomer (40.0 g), and 2-propanol (800 mL). The resulting solution was clear. Next, the reaction mixture was heated to 65° C. while being degassed with nitrogen. When the solution had reached 65° C., the catalyst, AIBN (1.50 g), was added. The solution immediately began to turn cloudy, indicating that polymerization was proceeding. The reaction was maintained at 65° C. for 6 hours, then cooled to 60° C. and stirred for an additional 18 hours. It was then allowed to cool to room temperature.

The resulting polymer was filtered and washed on the funnel with isopropanol, and then immediately slurried in 1000 mL of distilled water. The mixture was stirred for ½ hour and then 800 mL of methanol was added and the mixture was stirred for an additional ½ hour. The mixture was allowed to settle and the supernatant liquid was decanted, leaving a residue of about 750 mL. The residue was then slurried with an additional 750 mL of methanol and stirred for ½ hour. The methanol slurry and decantation process was repeated two more times with 800 mL of methanol each time. Next, 800 mL of isopropanol was added and the mixture was stirred for ½ hour and then filtered. Finally, 600 mL of isopropanol was added and the mixture was stirred for ½ hour. Filtration and vacuum drying afforded 49.2 g, 49.2% of the title polymer.

TMAEAC co-Sty (31%) crosslinked with 8% divinylbenzene crosslinking co-monomer and TMAEAC co-Sty (46%) crosslinked with 6% divinylbenzene crosslinking co-monomer were prepared in analogous fashion by varying the ratio of starting monomers.

11. Preparation of Poly(trimethylammoniumethylmethacrylatechloride co-poly(styrene) (TMAEMC co-Sty)

To a 1000 mL, three-necked, round-bottomed flask was added the following: trimethylammoniumethylmethacrylatechloride (TMAEMAC) (38.8 mL of a 50% aqueous solution, 21.7 g), divinyl benzene crosslinking co-monomer (3.72 g), styrene co-monomer (15.66 g), and 2-propanol (2500 mL). The resulting solution was clear. Next, the reaction mixture was heated to 65° C. while being degassed with nitrogen. When the solution had reached 65° C., the catalyst, AIBN (0.50 g), was added. The solution immediately began to turn cloudy, indicating that polymerization was proceeding. After two hours, the mixture became very thick and an additional 100 mL of isopropanol was added. After five hours the mixture was again very thick so an additional 100 mL of isopropanol was added. The reaction was maintained at 65° C. for 6 hours, and then allowed to cool to room temperature.

The resulting polymer was filtered and washed on the funnel with isopropanol, and then immediately slurried in 1000 mL of distilled water. The mixture was stirred for ½ hour and then transferred to a blender and blended for five minutes. The polymer slurry was filtered and 1000 mL of distilled water was added and the mixture was stirred for ½ hour. The mixture was filtered and the filter cake was slurried two times in 500 mL of methanol each time. Filtration and vacuum drying afforded 30.2 g, 75.9% of the title polymer.

TMAEMC co-Sty (58%) crosslinked with 4% divinylbenzene crosslinking co-monomer, TMAEMC co-Sty (33%) crosslinked with 4% divinylbenzene crosslinking co-monomer, and TMAEMC co-Sty (24%) crosslinked with 4% divinylbenzene crosslinking co-monomer were prepared in analogous fashion by varying the ratio of starting monomers.

12. Preparation of Poly(methacrylamidopropyl-3-(trimethylammonium) (chloride), co-(poly 2, 3, 4, 5, 6-pentafluorostyrene) (MAPTAC co-StyF$_5$)

To a 1000 mL, three-necked, round-bottomed flask was added the following: methacrylamidopropyl-3-(trimethylammonium) chloride (MAPTAC) (24.5 mL of a 50% aqueous solution, 13.00 g), divinylbenzene crosslinking co-monomer (1.00 g), pentafluorostyrene (6.00 g), 2-propanol (150 mL), and AIBN (0.50 g). The resulting solution was clear. Next, the reaction mixture was heated to 65° C. while being degassed with nitrogen. After a short period of time, the solution began to turn cloudy, indicating that polymerization was proceeding. After five hours the mixture was very thick so an additional 100 mL of isopropanol was added. The reaction was maintained at 65° C. for 24 hours, and then allowed to cool to room temperature.

The resulting polymer was filtered and washed on the funnel with isopropanol and immediately slurried in 500 mL of distilled water. The mixture was stirred for ½ hour. The polymer slurry was filtered and 500 mL of distilled water was added and the mixture was stirred for ½ hour. The mixture was filtered and the filter cake was slurried two times in 300 mL of methanol each time. Filtration and air drying afforded 7.74 g of the title co-polymer.

MAPTAC co-StyF$_5$ (20%) crosslinked with 5% divinylbenzene crosslinking co-monomer, MAPTAC co-StyF$_5$ (40%) crosslinked with 5% divinylbenzene crosslinking co-monomer, and MAPTAC co-StyF$_5$ (45%) crosslinked with 5% divinylbenzene crosslinking co-monomer were prepared in analogous fashion by varying the ratio of starting monomers.

13. Preparation of poly(methacrylamidopropyl-3-(trimethylammonium) chloride), co-poly 2-(trimethylammonium) ethyl methacrylate chloride, co-styrene (MAPTAC co-TMAEMC co-Sty)

To a 1000 mL, three-necked, round-bottomed flask was added the following: methacrylamidopropyl-3-(trimethylammonium) chloride (MAPTAC) (10.40 g of a 50% aqueous solution, 5.20 g), 2-(trimethylammonium) ethyl methacrylate chloride (TMAEMC) (4.86 g of a 70% aqueous solution, 3.40 g) divinylbenzene crosslinking co-monomer (1.00 g), styrene (10.40 g), 2-propanol (150 mL), and AIBN (0.50 g). The resulting solution was clear. Next, the reaction mixture was heated to 70° C. while being degassed with nitrogen. After a short period of time, the solution began to turn cloudy, indicating that polymerization was proceeding. The reaction was maintained at 70° C. for 24 hours, and then allowed to cool to room temperature.

The resulting polymer was filtered and washed on the funnel with isopropanol and immediately slurried in 500 mL of methanol. The mixture was stirred for ½ hour. The polymer slurry was filtered and 400 mL of distilled water was added and the mixture was stirred for ½ hour. The mixture was filtered and the water slurry was repeated. The mixture was filtered and the filter cake was slurried two times in 400 mL of methanol each time. Filtration and air drying afforded 5.39 g of the title co-polymer.

MAPTAC co-TMAEMC (34%) co-Sty (36%) crosslinked with 5% divinylbenzene crosslinking co-monomer, MAPTAC co-TMAEMC (31%) co-Sty (41%) crosslinked with 5% divinylbenzene crosslinking co-monomer, MAPTAC co-TMAEMC (28%) co-Sty (46%) crosslinked with 5% divinylbenzene crosslinking co-monomer, MAPTAC co-TMAEMC (23%) co-Sty (48%) crosslinked with 5% divinylbenzene crosslinking co-monomer, MAPTAC co-TMAEMC (26%) co-Sty (52%) crosslinked with 4% divinylbenzene crosslinking co-monomer, MAPTAC co-TMAEMC (17%) co-Sty (53%) crosslinked with 4% divinylbenzene crosslinking co-monomer, MAPTAC co-TMAEMC (15%) co-Sty (55%) crosslinked with 4% divinylbenzene crosslinking co-monomer, and MAPTAC co-TMAEMC (13%) co-Sty (61.5%) crosslinked with 4% divinylbenzene crosslinking co-monomer were prepared in analogous fashion by varying the ratio of starting monomers.

14. Preparation of Poly(trimethylammoniumethylmethacrylatechloride co-poly (isopropylacrylamide)) (TMAEMAC co-IPA)

The co-monomer isopropylacrylamide (IPA) was first prepared as follows.

Acryloyl chloride (63 mL, 70.2 g, 0.775 mol) was dissolved in tetrahydrofuran (200 mL) in a 1 L flask and placed in an ice bath. A solution containing isopropylamine (127.7 mL, 88.67 g, 1.50 mol) was added dropwise, maintaining the temperature at 5°–15° C. After addition the solution was stirred for 10 min and the solid isopropylamine hydrochloride was filtered off and discarded. The solvent was removed in vacuo from the mother liquor and the resulting almost colorless oil, which solidified on standing, was used without further purification to prepare the title co-polymer as follows.

To a 1000 mL, three-necked, round-bottomed flask was added the following: trimethylammoniumethylacrylate chloride (76.5 mL of a 50% aqueous solution, 41.18 g, 0.213 mol), methylene bis acrylamide crosslinking co-monomer (2.40 g), IPA co-monomer (4.52 g, 0.070 mol), and water (200 mL). The resulting solution was clear. The reaction mixture was stirred while being degassed with nitrogen. When the solution had been degassed, the catalyst, consisting of potassium persulfate (0.3 g) and potassium metabisulfate (0.3 g) was added. The polymerization initiated after 2 minutes and gelled after 3 minutes.

The next morning the gel was transferred to a blender and 1000 mL of water was added. After blending for a few seconds, the polymer had swelled to take up all of the water.

The swollen polymer was blended in several portions with isopropanol several times to dehydrate it. The resulting polymer was filtered and washed on the funnel with isopropanol and vacuum dried to afford 36.8 g of the title co-polymer.

15. Preparation of Poly(methacrylamidopropyl-3-(trimethylammonium chloride)) co-poly(vinyl pyridine) (MAPTAC co-VP)

To a 1000 mL, three-necked, round-bottomed flask was added the following: methacrylamidopropyl-3-(trimethylammonium) chloride (MAPTAC) (40 mL of a 50% aqueous solution, 21.0 g), divinyl benzene crosslinking co-monomer (2.25 g), vinyl pyridine (14.0 g, 0.133 mol), conc. hydrochloric acid (11 mL, 0.133 mol), 2-propanol (300 mL), and AIBN (0.67 g). The resulting solution was clear. Next, the reaction mixture was heated to 60° C. while being degassed with nitrogen. After a short period of time, the solution began to turn cloudy, indicating that polymerization was proceeding. The reaction was maintained at 60° C. for 20 hours, and then allowed to cool to room temperature.

The resulting polymer was filtered and washed on the funnel with isopropanol and immediately slurried in 1000 mL of distilled water. The mixture was stirred for 1 hour. The polymer slurry was filtered, washed on the funnel with methanol, and then slurried in 600 mL of methanol for one hour. Filtration and air drying afforded 20.4 g of copolymer.

16. Preparation of Poly(trimethylammoniumethylmethacrylate chloride) co-poly(p-fluorostyrene) (TMAEMC co-$F_1$Sty)

To a 500 mL flask was added the following: trimethylammoniumethylmethacrylate chloride (TMAEMC) (11.0 g of a 70% aqueous solution, 7.70 g), divinylbenzene crosslinking co-monomer (0.50 g), p-fluorostyrene co-monomer (4.00 g), 2-propanol (125 mL) and AIBN (0.25 g). The resulting solution was clear. Next, the reaction mixture was heated to 65° C. while being degassed with nitrogen. The solution immediately began to turn cloudy, indicating that polymerization was proceeding. The reaction was maintained at 65° C. for 6 hours, and then allowed to cool to room temperature.

The solvent was removed by decantation and the polymer was immediately slurried in 250 mL of distilled water. The mixture was stirred for ½ hour and then decanted. The water slurry was repeated three more times. Finally, the polymer was slurried in 400 mL of methanol. Filtration and vacuum drying afforded 5.42 g, 44.4% of the title copolymer.

TMAEMC co-$F_1$Sty (24%) crosslinked with 4% divinylbenzene crosslinking co-monomer was prepared in analogous fashion by varying the ratio of the starting monomers.

17. Preparation of Poly(methacrylamidopropyl-3-(trimethyl ammonium chloride)) co -poly (hexafluorobutyl methacrylate) (MAPTAC co$F_6$BMA)

To a 1000 mL, three-necked, round-bottomed flask was added the following: methacrylamidopropyl-3-(trimethylammonium) chloride (MAPTAC) (28.5 mL of a 50% aqueous solution, 15.0 g), divinylbenzene crosslinking co-monomer (1.00 g), hexafluorobutyl methacrylate (4.00 g), 2propanol (150 mL), and AIBN (0.50 g). The resulting solution was clear. Next, the reaction mixture was heated to 60° C. while being degassed with nitrogen. After a short period of time, the solution began to turn cloudy, indicating that polymerization was proceeding. The reaction was maintained at 60° C. for 24 hours, and then allowed to cool to room temperature.

The resulting polymer was filtered and washed on the funnel with isopropanol and immediately slurried in 500 mL of distilled water. The mixture was stirred for 1 hour. The polymer slurry was filtered and the water slurry was repeated one more time. The polymer was then slurried in 500 mL of methanol for one hour and filtered. The methanol slurry was repeated one more time. Finally the polymer was slurried in 400 mL of isopropanol and stirred overnight. Filtration and air drying afforded 7.52 g of the title copolymer.

18. Preparation of Poly(trimethylammoniumethylacrylate chloride) co-poly (hexafluoroisopropyl acrylate) (TMAEAC co-$F_6$IA)

To a 1000 mL, three-necked, round-bottomed flask was added the following: trimethylammoniumethylacrylate chloride (30.0 mL of a 50% aqueous solution, 15.0 g), divinylbenzene crosslinking co-monomer (1.00 g), $F_6$IPA co-monomer (4.00 g), AIBN (0.50 g), and isopropanol (150 mL). The resulting solution was clear. The reaction mixture was stirred while being degassed with nitrogen and heated to 60° C. After 18 hours the reaction mixture was allowed to cool to room temperature and the solvent was removed by decanting. The residual polymer was slurried in 400 mL of water, stirred for one hour and filtered. The water slurry was repeated one more time. Next the polymer was slurried two times in methanol. Finally, the polymer was slurried in 200 mL of isopropanol, stirred for two hours and filtered. Air drying afforded 5.59 g of the title polymer.

19. Preparation of Poly(methacrylamidopropyl-3-(trimethyl ammonium chloride) ) co -poly (heptadecafluorodecyl methacrylate) (MAPTAC co$F_{17}$DecMA)

To a 1000 mL, three-necked, round-bottomed flask was added the following: methacrylamidopropyl-3-(trimethylammonium) chloride (MAPTAC) (28.5 mL of a 50% aqueous solution, 15.0 g), divinylbenzene crosslinking co-monomer (1.00 g), heptadecafluorodecyl methacrylate (4.00 g), 2-propanol (150 mL), and AIBN (0.40 g). The resulting solution was clear. Next, the reaction mixture was heated to 65° C. while being degassed with nitrogen. After a short period of time, the solution began to turn cloudy, indicating that polymerization was proceeding. After four hours, the reaction mixture had gotten very thick and 100 mL more isopropanol was added. The reaction was maintained at 65° C. for 18 hours, and then allowed to cool to room temperature.

The resulting polymer was filtered and washed on the funnel with isopropanol and immediately slurried in 600 mL of distilled water. The mixture was stirred for 1 hour. The polymer slurry was filtered and the water slurry was repeated one more time. The polymer was then slurried in 500 mL of methanol for one hour and filtered. Air drying afforded 17.73 g of co-polymer.

20. Preparation of poly(methacrylamidopropyl-3-(trimethylammonium chloride)), co-poly (2-(trimethylammonium) ethyl acrylate chloride), co -poly styrene (MAPTAC co-TMAEAC co-Sty)

To a 1000 mL, three-necked, round-bottomed flask was added the following: methacrylamidopropyl-3-(trimethylammonium) chloride (MAPTAC) (10.00 g of a 50% aqueous solution, 5.00 g), 2-(trimethylammonium) ethyl methacrylate chloride (TMAEAC) (6.00 g of a 50% aqueous solution, 3.00 g) divinylbenzene crosslinking co-monomer (1.00 g), styrene (11.00 g), 2-propanol (150 mL), and AIBN (0.25 g). The resulting solution was clear. Next, the reaction mixture was heated to 70° C. while being degassed with nitrogen. After a short period of time, the solution began to turn cloudy, indicating that polymerization was proceeding. The reaction was maintained at 70° C. for 24 hours, and then allowed to cool to room temperature.

The resulting polymer was filtered and washed on the funnel with isopropanol and immediately slurried in 500 mL of methanol. The mixture was stirred for ½ hour. The polymer slurry was allowed to settle and decanted. 200 mL of distilled water was added and the mixture was stirred for ½ hour. The mixture was decanted and the water slurry was repeated with 400 mL. The mixture was decanted and the polymer was slurried two times in 200 mL of methanol each time. Filtration and air drying afforded 2.76 g of the title co-polymer.

MAPTAC co-TMAEAC (10%) co-Sty (60%) crosslinked with 5% divinylbenzene crosslinking co-monomer was prepared in analogous fashion by varying the ratio of starting monomers.

21. Preparation of poly (2-(trimethylammonium) ethyl acrylate chloride) co-poly (2,3,4,5,6-pentafluorostyrene) (TMAEAC co-StyF$_5$)

To a 1000 mL, three-necked, round-bottomed flask was added the following: 2-(trimethylammonium) ethyl acrylate chloride (TMAEAC) (24.0 mL of a 50% aqueous solution, 13.00 g), divinylbenzene crosslinking co-monomer (1.00 g), pentafluorostyrene (6.00 g), 2-propanol (150 mL), and AIBN (0.50 g). The resulting solution was clear. Next, the reaction mixture was heated to 65° C. while being degassed with nitrogen. After a short period of time, the solution began to turn cloudy, indicating that polymerization was proceeding. After two hours the mixture was very thick so an additional 100 mL of isopropanol was added. The reaction was maintained at 65° C. for 22 hours, and then allowed to cool to room temperature.

The resulting polymer was filtered and washed on the funnel with isopropanol and immediately slurried in 400 mL of distilled water. The mixture was stirred for ½ hour. The polymer slurry was filtered and 600 mL of distilled water was added and the mixture was stirred for ½ hour. The mixture was filtered and the filter cake was slurried in 400 mL of methanol. Filtration and air drying afforded 7.26 g of the title co-polymer.

TMAEAC co-StyF$_5$ (20%) crosslinked with 5% divinylbenzene crosslinking co-monomer was prepared in analogous fashion by varying the ratio of starting monomers.

22. Preparation of poly (2-(trimethylammonium) ethyl methacrylate chloride), co-poly (2,3,4,5,6-pentafluorostyrene) (TMAEMC co-StyF$_5$)

To a 1000 mL, three-necked, round-bottomed flask was added the following: 2-(trimethylammonium) ethyl methacrylate chloride (TMAEMC) (19.52 of a 70% aqueous solution, 13.66 g), divinylbenzene crosslinking co-monomer (1.00 g), pentafluorostyrene (9.18 g), 2-propanol (150 mL), and AIBN (0.40 g). The resulting solution was clear. Next, the reaction mixture was heated to 70° C. while being degassed with nitrogen. After a short period of time, the solution began to turn cloudy, indicating that polymerization was proceeding. After 1.5 hours the mixture was very thick so an additional 50 mL of isopropanol was added. The reaction was maintained at 70° C. for 5 hours, and then allowed to cool to room temperature.

The resulting polymer was filtered and washed on the funnel with isopropanol and immediately slurried in 500 mL of distilled water. The mixture was stirred for ¼ hour. The polymer slurry was filtered and 500 mL of distilled water was added and the mixture was stirred for ¼ hour. The water slurry was repeated one more time. The mixture was filtered and the filter cake was slurried three times in 300 mL of methanol each time. Filtration and air drying afforded 1.26 g of the title co-polymer.

TMAEMC co-StyF$_5$ (24%) crosslinked with 4% divinylbenzene crosslinking co-monomer and TMAEMC co-StyF$_5$ (39%) crosslinked with 4% divinylbenzene crosslinking co-monomer were prepared in analogous fashion by varying the ratio of starting monomers.

23. Preparation of Poly(ethyleneimine)

Polyethyleneimine (120 g of a 50% aqueous solution; Scientific Polymer Products) was dissolved in water (250 mL). Epichlorohydrin (22.1 mL) was added dropwise. The solution was heated to 60° C. for 4 h, after which it had gelled. The gel was removed, blended with water (1.5 L) and the solid was filtered off, rinsed three times with water (3 L) and twice with isopropanol (3 L), and the resulting gel was dried in a vacuum oven to yield 81.2 g of the title polymer.

24. Preparation of Poly(methacrylamidopropyl-3-(trimethylammonium chloride) ), co-poly(2-(trimethylammonium) ethylmethacrylate chloride) ) co-poly (2,3,4,5,6-pentafluorostyrene) (MAPTAC co -TMAEMC co-StyF$_5$)

To a 1000 mL, three-necked, round-bottomed flask was added the following: methacrylamidopropyl-3-(trimethylammonium) chloride (MAPTAC) (10.00 of a 50% aqueous solution, 5.00 g), 2-(trimethylammonium) ethyl methacrylate chloride (TMAEMC) (5.71 g of a 70% aqueous solution, 4.00 g), divinylbenzene crosslinking co-monomer (1.00 g), pentafluorostyrene (10.00 g), 2-propanol (150 mL), and AIBN (0.50 g). The resulting solution was clear. Next, the reaction mixture was heated to 70° C. while being degassed with nitrogen. After a short period of time, the solution began to turn cloudy, indicating that polymerization was proceeding. The reaction was maintained at 70° C. for 24 hours, and then allowed to cool to room temperature.

The resulting polymer was filtered and washed on the funnel with isopropanol and immediately slurried in 500 mL of methanol. The mixture was stirred for ¼ hour. The polymer slurry was filtered and then slurried 3 times in 300 mL of water each time. The last time the polymer slurry was blended for 5 minutes. The mixture was filtered and the filter cake was slurried two times in 300 mL of methanol each time. Filtration and vacuum drying afforded 9.74 g of co-polymer.

25. Preparation of poly (2-(trimethylammonium) ethyl acrylate chloride), co-poly (2-(trimethylammonium) ethylmethacrylate chloride) co-styrene (TMAEAC, co-TMAEMC, co-Sty)

To a 1000 mL, three-necked, round-bottomed flask was added the following: 2-(trimethylammonium) ethyl acrylate chloride (TMAEAC) (6.00 g of a 50% aqueous solution, 3.00 g), 2-(trimethylammonium) ethyl methacrylate chloride (TMAEMC) (4.29 g of a 70% aqueous solution, 3.00 g), divinylbenzene crosslinking co-monomer (1.00 g), styrene (13.00 g), 2-propanol (150 mL), and AIBN (0.50 g). The resulting solution was clear. Next, the reaction mixture was heated to 70° C. while being degassed with nitrogen. After a short period of time, the solution began to turn cloudy, indicating that polymerization was proceeding. The reaction was maintained at 70° C. for 24 hours, and then allowed to cool to room temperature.

The resulting polymer was decanted and immediately slurried in 500 mL of methanol. The mixture was stirred for ½ hour. The polymer slurry was filtered and 500 mL of distilled water was added. The mixture was then stirred for ½ hour and blended for 10 minutes. The mixture was allowed to settle and the water was decanted. The water slurry was repeated two more times and the decantation residue was slurried two times in 400 mL of methanol each time, settling and decanting each time. Vacuum drying afforded 8.03 g of the title co-polymer.

26. Preparation of Poly(methacrylamidopropyl-3-(trimethylammonium) chloride), co-poly(2-(trimethylammonium) ethylacrylate chloride) co-poly (2,3,4,5,6-pentafluorostyrene) (MAPTAC co -TMAEAC co-StyF$_5$)

To a 1000 mL, three-necked, round-bottomed flask was added the following: methacrylamidopropyl-3-(trimethylammonium) chloride (MAPTAC) (8.00 g of a 50% aqueous solution, 4.00 g), 2-(trimethylammonium) ethyl acrylate chloride (TMAEMA) (6.00 g of a 50% aqueous solution, 3.00 g), divinylbenzene crosslinking co-monomer (1.00 g), pentafluorostyrene (12.00 g), 2-propanol (150 mL), and AIBN (0.50 g). The resulting solution was clear. Next, the reaction mixture was heated to 70° C. while being degassed with nitrogen. After a short period of time, the solution began to turn cloudy, indicating that polymerization was proceeding. The reaction was maintained at 70° C. for 24 hours, and then allowed to cool to room temperature.

The resulting polymer was filtered and washed on the funnel with isopropanol and immediately slurried in 400 mL of methanol. The mixture was stirred for ½ hour. The polymer slurry was filtered and then slurried 2 times in 250 mL of water each time. The last time the polymer slurry was blended for 5 minutes. The mixture was filtered and the filter cake was slurried two times in 250 mL of methanol each time. Filtration and vacuum drying afforded 7.80 g of co-polymer.

27. Preparation of Poly ((trimethylammonium) ethyl acrylate chloride), co-poly(2-(trimethylammonium) ethyl-methacrylate chloride) co-poly (2,3,4,5,6-pentafluorostyrene) (TMAEAC, co-TMAEMC, co-StyF$_5$ )

To a 1000 mL, three-necked, round-bottomed flask was added the following: 2-(trimethylammonium) ethyl acrylate chloride (TMAEAC) (6.00 g of a 50% aqueous solution, 3.00 g), 2-(trimethylammonium) ethyl methacrylate chloride (TMAEMC) (4.29 g of a 70% aqueous solution, 3.00 g), divinylbenzene crosslinking co-monomer (1.00 g), pentafluorostyrene (13.00 g), 2-propanol (150 mL), and AIBN (0.50 g). The resulting solution was clear. Next, the reaction mixture was heated to 70° C. while being degassed with nitrogen. After a short period of time, the solution began to turn cloudy, indicating that polymerization was proceeding. The reaction was maintained at 70° C. for 24 hours, and then allowed to cool to room temperature.

The resulting polymer was decanted and immediately slurried in 400 mL of methanol. The mixture was stirred for ½ hour. The polymer slurry was filtered and then slurried two times in 200 mL of water each time. The second time the polymer slurry was blended for 5 minutes. The mixture was filtered and the filter cake was slurried two times in 200 mL of methanol each time. Vacuum drying afforded 6.87 g of co-polymer.

28. Preparation of Poly (methacrylamidopropyltrimethylammonium chloride) co-poly (4-vinylbiphenyl) (MAPTAC co-VBPh)

To a 1000 mL, three-necked, round-bottomed flask was added the following: methacrylamidopropyltrimethylammonium chloride (MAPTAC) (10.49 g of a 50% aqueous solution, 0.0475 mol), 4-vinylbiphenyl (VBPh) (9.01 g, 0.050 mol), divinyl benzene crosslinking co-monomer (1.47 g), 2-propanol (150 mL), and the polymerization initiator AIBN (0.25 g). The resulting mixture contained insoluble VBPh which dissolved upon warming. Next, the reaction mixture was heated to 70° C. while degassing with nitrogen. After a short period of time, the solution began to turn cloudy, indicating that polymerization was proceeding. The reaction was maintained at 70° C. for 24 hours and then filtered while hot.

The resulting polymer was washed on the filtration funnel with isopropanol, and then immediately slurried in 200 mL of methanol, followed by stirring for 1 hour. The polymer slurry was then filtered, after which the methanol slurry procedure was repeated. Next, the polymer was slurried two times using 200 mL of water each time. The resulting mixture was then filtered and the filter cake slurried two times with methanol using 200 mL of methanol each time. The resulting mixture was then filtered and vacuum dried to afford 9.59 g of copolymer.

29. Preparation of Poly (methacrylamidopropyltrimethylammonium chloride) co-poly (4-vinylanisole) (MAPTAC co-VA)

To a 1000 mL, three-necked, round-bottomed flask was added the following: methacrylamidopropyltrimethylammonium chloride (MAPTAC) (10.49 g of a 50% aqueous solution, 0.0475 tool), 4-4-vinylanisole (VA) (6.71 g, 0,050 tool), divinyl benzene crosslinking co-monomer (1.30 g), 2-propanol (200 mL), and the polymerization initiator AIBN (0.40 g). The resulting clear solution was heated to 70° C. while degassing with nitrogen. After several hours the solution began to turn cloudy, indicating that polymerization was proceeding. The reaction was maintained at 70° C. for 36 hours and then allowed to cool to room temperature.

The resulting polymer was filtered and washed on the filtration funnel with isopropanol, and then immediately slurried in 200 mL of methanol, followed by stirring for 1 hour. The polymer slurry was then filtered and slurried two times using 200 mL of water each time. The resulting mixture was then filtered and the filter cake slurried in 200 mL of methanol, after which it was slurried in 200 mL of isopropanol. The resulting mixture was then filtered and vacuum dried to afford 5.19 g of copolymer.

30. Preparation of Poly (N-(4-methylstyrene)-N'-(3-trimethylammonio-2-hydroxypropylchloride)piperazine)

The first step in the reaction is the preparation of 4-(piperazinylmethyl)styrene.

To a 500 mL flask was added vinylbenzyl chloride (7.63 g, 0.050 mol), piperazine (8.61 g, 0.100 mol), and isopropanol (50 mL). The resulting solution was heated to 70° C. for 45 minutes and then cooled slowly to room temperature to form a slurry of crystalline material. The slurry was refrigerated for about three hours and then filtered. The solid piperazine hydrochloride salt was vacuum dried and then weighed (5.55 g) and discarded. The mother liquor was concentrated to about 25 mL on a rotary evaporator and ethyl acetate (50 mL) was added). The resulting mixture was refrigerated for about 10 minutes, after which a second crop of piperazine hydrochloride was filtered off and discarded. The mother liquor was then evaporated to dryness on a rotary evaporator to afford 10.35 g of crude 4-(piperazinylmethyl)styrene which was used without further purification to prepare N-(4-methylstyrene)-N'-(3-trimethylammonio-2-hydroxypropyl chloride)piperazine as follows.

To a 500 mL flask was added 4-(piperazinylmethyl) styrene (10.35 g, about 0.45 mol), glycidyl trimethyl ammonium chloride (7.58 g, 0.045 mol), and isopropanol (50 mL). The resulting mixture was heated to 60° C. and stirred for 20 hours, after which it was cooled to room temperature and used for polymerization reactions without further purification as follows.

To 0.40 mol of N-(4-methylstyrene)-N'-(3-trimethylammonio-2-hydroxypropyl chloride)piperazine in 100 mL of isopropanol was added divinyl benzene crosslinking co-monomer (0.93 g). The resulting solution was degassed with nitrogen and then the polymerization initiator AIBN (0.20 g) was added. The temperature was raised to 70° C. with continued nitrogen degassing and held there for three hours, at which point a large quantity of cross-linked polymer had precipitated. The mixture was then cooled to 40° C. and filtered.

The resulting polymer was washed on the filtration funnel with isopropanol and then immediately slurried in 200 mL of methanol, after which it was stirred for 1 hour. The polymer slurry was then filtered and the methanol slurry procedure repeated. The resulting polymer was then slurried two times in 200 mL of water each time, followed by filtration. The filter cake was slurried two times in 200 mL of methanol each time. Filtration and vacuum drying afforded 7.90 g of polymer.

31. Preparation of Poly (N-(4-methylstyrene)-N'-(3-trimethylammonio-2-hydroxypropyl)piperazine), co-polystyrene To 0.022 mol of N-(4-methylstyrene)-N'-(3-trimethylammonio-2-hydroxypropyl)piperazine (prepared as described in Example 30) was added styrene co-monomer (2.29 g, 0.022 mol) and divinyl benzene crosslinking co-monomer (0.50 g, 0.004 mol). The resulting solution was degassed with nitrogen, after which the polymerization initiator AIBN (0.3 g) was added. The temperature was raised to 70° C. with continued nitrogen degassing and held there for four hours, at which point a large quantity of crosslinked polymer has precipitated. Twenty five mL's of additional isopropanol was then added and heating continued for another 19 hours, after which the mixture was cooled to room temperature and filtered to yield solid polymer.

The resulting polymer was filtered and washed on the filtration funnel with methanol and then immediately slurried in 200 mL of methanol. The mixture was stirred for 0.5 hour, after which it was filtered and the polymer slurried two times using 250 mL of water each time. Next, the mixture was filtered and the filter cake was slurried in 200 mL of methanol, filtered, and then slurried in 200 mL of isopropanol. Filtration and vacuum drying afforded 4.98 g of copolymer.

A copolymer containing a 2:1 molar ration of styrene to quaternary amine monomer was also prepared in an analogous manner.

32. Preparation of Poly (N-(3-trimethylammonio-2-hydroxypropylchloride)-4-aminostyrene)

The first step is the preparation of 4-aminomethylstyrene as follows.

To a 250 mL flask was added vinylbenzyl chloride (7.63 g, 0.050 mol), concentrated aqueous ammonia (9.8 mL), and isopropanol (40 mL). The mixture was stirred for one week, at which point a large quantity of crystalline material (ammonium chloride) had precipitated. The solid was filtered off and washed with isopropanol. The mother liquor was evaporated on a rotary evaporator until no ammonia odor could be detected. Isopropanol (50 mL) was then added, and the mixture refrigerated for several hours. Following refrigeration, ammonium chloride which had precipitated was filtered off to yield 4-aminomethylstyrene which was used without further purification.

To a 500 mL flask was added 4-aminomethylstyrene (0.050 mol), glycidyl trimethylammonium chloride (7.62 g, 0.050 mol), water (about 2 mL) to effect solution, and divinylbenzene crosslinking co-monomer (0.98 g). The resulting solution was heated at 70° C. for 5 hours, after which a small amount of water (about 5–10 mL) was added to dissolve some precipitated salts. The polymerization initiator AIBN (0.20 g) was added while concurrently degassing the solution with nitrogen. The reaction mixture became very thick with polymer, requiring the addition of isopropanol to permit stirring.

After stirring for about 16 hours at 70°0 C., the mixture was cooled to room temperature and filtered. The resulting polymer was washed on the filtration funnel with methanol and then immediately slurried in 200 mL of methanol. The resulting mixture was stirred for 1 hour, after which the polymer slurry was filtered and the methanol slurry procedure repeated. The polymer was then slurried two times in 200 mL of water each time, after which the mixture was filtered and the filter cake slurried in 200 mL of methanol. Filtration and vacuum drying afforded 8.68 g of polymer.

33. Alkylation of Poly(dimethylaminopropylmethacrylamide) crosslinked with methylenebismethacrylamide with 1-iodooctane alkylating agent Poly(dimethylaminopropylmethacrylamide) crosslinked with methylenebismethacrylamide prepared as described in Example 5 (1.0 g) was suspended in methanol (100 mL) and sodium hydroxide (0.2 g) was added. After stirring for 15 minutes, 1-iodooctane (1.92 mL) was added and the mixture stirred at 60° C. for 20 hours. The mixture was then cooled and the solid filtered off. Next, the solid was washed by suspending it in isopropanol (500 mL), after which it was stirred for 1 hour and then collected by filtration. The wash procedure was then repeated twice using aqueous sodium chloride (500 mL of a 1M solution), twice with water (500 mL), and once with isopropanol (500 mL) before drying in a vacuum oven at 50° C. for 24 hours to yield 0.1 g of alkylated product.

34. Alkylation of Poly(dimethylaminopropylacrylamide) crosslinked with methylenebismethacrylamide with 1-iodooctane alkylating agent Poly(dimethylaminopropylacrylamide) crosslinked with methylenebismethacrylamide prepared as described in Example 4 (10 g) was alkylated according to the procedure described in Example 33. The procedure yielded 2.95 g of alkylated product.

35. Preparation of Poly (2-(methacroylamido)ethyltrimethylammonium iodide) co-polystyrene The first step is the preparation of 2-(N',N'-dimethylamino)-N-ethyl methacrylamide hydrochloride as follows.

To a 1000 mL flask was added methacryloyl chloride (52.3 g, 0.5 mol) and tetrahydrofuran (300 mL). The solution was cooled to less than 10° C. after which a solution of N,N-dimethylaminoethylamine (30.5 g, 0.35 mol) in tetrahydrofuran (100 mL) was added dropwise while maintaining the temperature at 8°–10° C. When the addition was complete, the mixture was filtered, washed with cold tetrahydrofuran, and vacuum dried to yield 65.69 g of 2-(N', N'-dimethylamino)-N-ethyl methacrylamide hydrochloride The next step was the preparation of 2-(methacryloylamido)ethyltrimethylammonium iodide as follows.

Potassium hydroxide (15.4 g, 0.24 mol) and methanol (240 mL) were added to a 500 mL flask, and the mixture stirred to effect complete dissolution of the potassium hydroxide To the solution was added 2-(N', N'-dimethylamino)-N-ethyl methacrylamide hydrochloride (46.35 g, 0.24 mol) and the resulting mixture stirred for 0.5 hour. The mixture was then filtered to remove potassium chloride and the filtrate was concentrated on a rotary evaporator. Isopropanol (400 mL) and methyl iodide (18.7 mL, 42.6 g, 0.30 mol) were added to the concentrated filtrate and the mixture stirred at room temperature overnight. In the morning, the solid product was filtered off, washed with isopropanol, and vacuum dried to yield 61.08 g of 2-(methacryloylamido)ethyltrimethylammonium iodide as a white crystalline solid.

Next, 2-(methacryloylamido)ethyltrimethylammonium iodide (12.24 g, 0.050 mol), styrene (5.2 g, 0.050 mol), divinylbenzene crosslinking co-monomer (0.65 g, 0.005 mol), isopropanol (150 mL), water (20 mL), and the polymerization initiator AIBN (0.4 g) were added to a 1000 mL flask and the resulting solution degassed with nitrogen while heating to 70° C. The solution was then stirred for 24 hours at 70° C. under nitrogen, after which it was cooled to room temperature. At this point, the solvent was decanted and 200 mL of methanol added to the flask to create a slurry which was stirred overnight. The product was then filtered and added to a blender with 500 mL of water. The resulting mixture was blended for 15 minutes and then filtered. The remaining solid material was washed sequentially with water (200 mL) and methanol (200 mL). Filtration and vacuum drying yielded 3.22 g of the title polymer.

Testing of Polymers

A. Preparation of Artificial Intestinal Fluid Test Procedure No. 1

Sodium carbonate (1.27 g) and sodium chloride (1.87 g) were dissolved in 400 mL of distilled water. To this solution was added a mixture of purified bile acids, consisting of taurocholic acid (0.138 g, 0.24 mmol), glycocholic acid (0.292 g, 0.60 mmol), glycodeoxycholic acid (0.085 mmol, 0.18 mmol) and glycochenodeoxycholic acid (0.085 mmol, 0.18 mmol). The pH of the solution was adjusted to 7.20 with acetic acid. This solution was used for the testing of the various polymers. The total bile salt concentration in this solution is 3 millimolar, a concentration approximately equal to that found in normal physiological solutions in the duodenum.

Polymers were tested as follows.

To a 40 mL centrifuge tube was added 0.25 g of polymer and 20 mL of the artificial small fluid prepared as described above. The mixture was stirred in a water bath maintained at 37° C. for three hours. The mixture was then centrifuged and the supernatant liquid, being slightly cloudy, was filtered. The filtrate was analyzed for total 3-hydroxy steroid content by an enzymatic assay using 3a-hydroxy steroid dehydrogenase, as described below.

Test Procedure No. 2

Sodium carbonate (1.27 g) and sodium chloride (1.87 g) were dissolved in 400 mL of distilled water. To this solution was added either glycocholic acid (1.95 g, 4.0 mmol) or glycochenodeoxycholic acid (1.89 g, 4.0 mmol) to make a 10 mM solution. The pH of the solution was adjusted to 6.8 with acetic acid. These stock solutions were used for the testing of the various polymers.

Polymers were tested as follows.

To a 14 mL centrifuge tube was added 10 mg of polymer and 10 mL of a bile salt solution in concentrations ranging from 0.1–10 mM prepared from 10 mM stock solution (prepared as described above) and buffer without bile salt in the appropriate amount. The mixture was stirred in a water bath maintained at 37° C. for three hours. The mixture was then filtered. The filtrate was analyzed for total 3-hydroxy steroid content by an enzymatic assay using 3a-hydroxy steroid dehydrogenase, as described below.

Enzymatic Assay for Total Bile Salt Content

Four stock solutions were prepared.

Solution 1. Tris-HCl buffer, containing 0.133M Tris, 0.666 mM EDTA at pH 9.5.

Solution 2. Hydrazine hydrate solution, containing 1M hydrazine hydrate at pH 9.5.

Solution 3. NAD+ solution, containing 7 mM NAD+ at pH 7.0.

Solution 4. HSD solution, containing 2 units/mL in Tris-HCl buffer (0.03M Tris, 1 mM EDTA) at pH 7.2.

To a 3 mL cuvette was added 1.5 mL of Solution 1, 1.0 mL of Solution 2, 0.3 mL of Solution 3, 0.1 mL of Solution 4 and 0.1 mL of supernatant/filtrate from a polymer test as described above. The solution was placed in a UV-VIS spectrophotometer and the absorbance (O.D.) of NADH at 340 nm was measured. The bile salt concentration was determined from a calibration curve prepared from dilutions of the artificial intestinal fluid prepared as described above.

All of the polymers previously described were tested in one or both of the above tests and all were efficacious in removing bile salts from the artificial intestinal fluid. Use The polymers according to the invention may be administered orally to a patient in a dosage of about 1 mg/kg/day to about 10 g/kg/day; the particular dosage will depend on the individual patient (e.g., the patient's weight and the extent of bile salt removal required). The polymer may be administrated either in hydrated or dehydrated form, and may be flavored if necessary to enhance patient acceptability; additional ingredients such as artificial coloring agents may be added as well.

Examples of suitable forms for administration include pills, tablets, capsules, and powders (for sprinkling on food). The pill, tablet, capsule, or powder can be coated with a substance capable of protecting the composition from the gastric acid in the patient's stomach for a period of time sufficient to allow the composition to pass undisintegrated into the patient's small intestine. The polymer may be administered alone or in combination with a pharmaceutically acceptable carrier substance, e.g., magnesium carbonate, lactose, or a phospholipid with which the polymer can form a micelle.

Other embodiments are within the following claims.

What is claimed is:

1. A method for removing bile salts from a patient by ion exchange comprising administering to said patient a therapeutically effective amount of one or more crosslinked polymers comprising (1) a monoreactive hydrophobic co-monomer and (2) a repeat unit having the formula

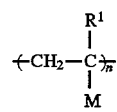

where n is an integer; $R^1$ is H or a $C_1$–$C_8$ alkyl group; M is

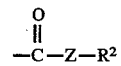

or —Z—$R^2$; Z is O, $NR^3$ S or $(CH_2)_m$; m=0–10; $R^3$ is H or a $C_1$–$C_8$ alkyl group; and $R^2$ is

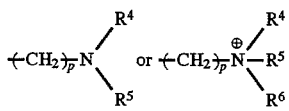

where p=0–10, and each $R^4$, $R^5$, and $R^6$, independently, is H, a $C_1$–$C_8$ alkyl group, or an aryl group, said polymers being non-toxic and stable once ingested.

2. The method of claim 1 wherein said polymer is crosslinked by means of a multifunctional crosslinking co-monomer, said co-monomer being present in an amount from about 0.5–25% by weight, based upon total monomer weight.

3. The method of claim 2 wherein said crosslinking co-monomer is present in an amount from about 1–10% by weight, based upon total monomer weight.

4. The method of claim 1 wherein said monoreactive hydrophobic co-monomer is selected from the group consisting of styrene and fluorinated derivatives thereof; vinyl naphthalene and fluorinated derivatives thereof; ethyl vinylbenzene and fluorinated derivatives thereof; N-alkyl and N-aryl derivatives of acrylamide and methacrylamide, and fluorinated derivatives thereof; alkyl and aryl acrylates and fluorinated derivatives thereof; alkyl and aryl methacrylates and fluorinated derivatives thereof; 4-vinylbiphenyl and fluorinated derivatives thereof; 4-vinylanisole and fluorinated derivatives thereof; and 4-aminostyrene and fluorinated derivatives thereof.

5. The method of claim 1 wherein said polymer further comprises one or more amine co-monomers.

6. The method of claim 5 wherein said amine co-monomer is vinyl pyridine, dimethylaminmethyl styrene, or vinyl imidazole.

7. The method of claim 1 wherein said repeat unit (2) has the formula

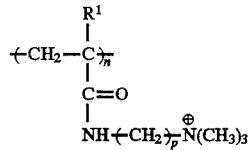

or copolymer thereof wherein $R^1$, n and p are as defined in claim 1.

8. The method of claim 7 wherein said monoreactive hydrophobic co-monomer is n-butylmethacrylamide, hexafluorobutylmethacrylate, heptadecafluorodecylmethacrylate, styrene or a fluorinated derivative thereof, 2-vinyl naphthalene, 4-vinyl imidazole, vinyl pyridine, 4-vinylbiphenyl or a fluorinated derivative thereof, 4-vinylanisole or a fluorinated derivative thereof, or 4-aminostyrene or a fluorinated derivative thereof.

9. The method of claim 11 wherein said polymer further comprises a co-monomer selected from the group consisting of trimethylammoniumethylmethacrylate and trimethylammoniumethylacrylate.

10. The method of claim 11 wherein said repeat unit (2) has the formula

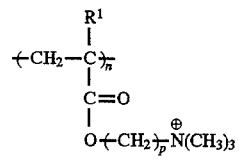

or copolymer thereof, wherein $R^1$, n and p are as defined in claim 1.

11. The method of claim 10 wherein said monoreactive hydrophobic co-monomer is isopropylacrylamide, styrene or a fluorinated derivative thereof or hexafluoroisopropylacrylate.

12. The method of claim 10 wherein said polymer further comprises, as a co-monomer, trimethylammoniumethylmethacrylate.

13. The method of claim 1 wherein said repeat unit (2) has the formula

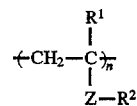

or copolymer thereof, wherein Z is $NR^3$ or $(CH_2)_m$, $R^2$ is

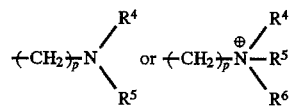

$R^1$, $R^3$, $R^4$, $R^5$, $R^6$, n, m and p are as defined in claim 1.

14. The method of claim 13 wherein said monoreactive hydrophobic co-monomer is selected from the group consisting of styrene and fluorinated derivatives thereof; vinyl naphthalene and fluorinated derivatives thereof; ethyl vinylbenzene and fluorinated derivatives thereof; N-alkyl and N-aryl derivatives of acrylamide and methacrylamide, and fluorinated derivatives thereof; alkyl and aryl acrylates and fluorinated derivatives thereof; alkyl and aryl methacrylates and fluorinated derivatives thereof; 4-vinylbiphenyl and fluorinated derivatives thereof; 4-vinylanisole and fluorinated derivatives thereof; and 4-aminostyrene and fluorinated derivatives thereof.

15. The method of claim 1 wherein said polymer further comprises one or more exchangeable counterions.

16. The method of claim 15 wherein at least one of said counterions is $Cl^-$, $Br^-$, $CH_3OSO_3^-$, $HSO_4^-$, $SO_4^{2-}$, $HCO_3^-$, $CO_3^{2-}$, acetate, lactate, succinate, propionate, butyrate, ascorbate, citrate, maleate, folate, an amino acid derivative, a nucleotide, a lipid, or a phospholipid.

17. A method for removing bile salts from a patient by ion exchange comprising administering to said patient a therapeutically effective amount of one or more crosslinked polymers comprising a repeat unit having the formula

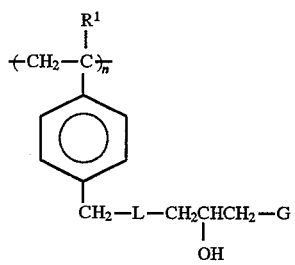

or copolymer thereof, where n is an integer; $R^1$ is H or a $C_1$–$C_8$ alkyl group; L is —NH—or

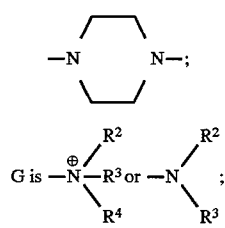

G is $-\overset{\oplus}{N}\begin{smallmatrix}R^2\\ \diagup\\ -R^3\\ \diagdown\\ R^4\end{smallmatrix}$ or $-N\begin{smallmatrix}R^2\\ \diagup\\ \\ \diagdown\\ R^3\end{smallmatrix}$ ;

and each $R^2$, $R^3$, and $R^4$, independently, is H, a $C_1$–$C_8$ alkyl group, or an aryl group, said polymers being non-toxic and stale once ingested.

18. The method of claim 17 wherein said polymer is crosslinked by means of a multifunctional crosslinking co-monomer, said co-monomer being present in an amount from about 0.5–25% by weight, based upon total monomer weight.

19. The method of claim 18 wherein said crosslinking co-monomer is present in an amount from about 1–10% by weight, based upon total monomer weight.

20. The method of claim 17 wherein said polymer further comprises one or more monoreactive hydrophobic co-monomers.

21. The method of claim 20 wherein said monoreactive hydrophobic co-monomer is selected from the group consisting of styrene and fluorinated derivatives thereof; vinyl naphthalene and fluorinated derivatives thereof; ethyl vinylbenzene and fluorinated derivatives thereof; N-alkyl and N-aryl derivatives of acrylamide and methacrylamide, and fluorinated derivatives thereof; alkyl and aryl acrylates and fluorinated derivatives thereof; alkyl and aryl methacrylates and fluorinated derivatives thereof; 4-vinylbiphenyl and fluorinated derivatives thereof; 4-vinylanisole and fluorinated derivatives thereof; and 4-aminostyrene and fluorinated derivatives thereof.

22. The method of claim 17 wherein said polymer comprising a repeat unit having the formula

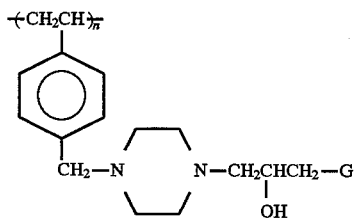

or copolymer thereof.

23. The method of claim 17 wherein said polymer comprising a repeat unit having the formula

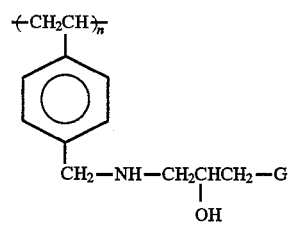

or copolymer thereof.

24. The therapeutic composition effective for removing bile salts by ion exchange comprising a therapeutic amount of a crosslinked polymer comprising a repeat unit having the formula

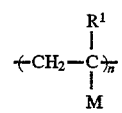

or copolymer thereof, where n is an integer; $R^1$ is H or a $C_1$–$C_8$ alkyl group; M is

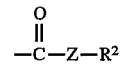

or —Z—$R^2$; Z is O NR$^3$, S, or (CH$_2$)$_m$; m=0–10; $R^3$ is H or a $C_1$–$C_8$ alkyl group; and $R^2$ is

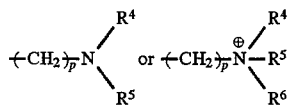

where p=0–10, and each $R^4$, $R^5$, and $R^6$, independently, is H, a $C_1$–$C_8$ alkyl group, or an aryl group, said polymer being non-toxic and stable once ingested.

25. A therapeutic composition effective for removing bile salts by ion exchange comprising a therapeutic amount of a crosslinked polymer comprising a repeat unit having the formula

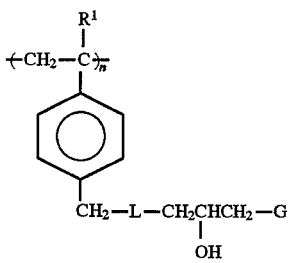

or copolymer thereof, where n is an integer; $R^1$ is H or a $C_1$–$C_8$ alkyl group; L is —NH—or

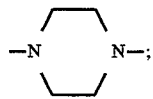

-continued

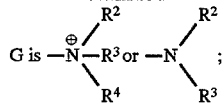

and each $R^2$, $R^3$, and $R^4$, independently, is H, a $C_1$–$C_8$ alkyl group, or an aryl group, said polymer being non-toxic and stable once ingested.

26. A crosslinked polymer composition comprising:

(1) a monoreactive hydrophobic co-monomer and
(2) a repeat unit having the formula

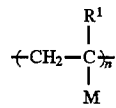

or copolymer thereof, where n is an integer; $R^1$ is H or a $C_1$–$C_8$ alkyl group; M is

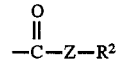

or —Z—$R^2$; Z is O, $NR^3$, S, or $(CH_2)_m$; m=0–10; $R^3$ is H or a $C_1$–$C_8$ alkyl group; and $R^2$ is

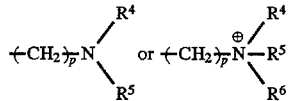

where p=0–10 and each $R^4$, $R^5$, and $R^6$ independently, is H, a $C_1$–$C_8$ alkyl group, or an aryl group.

27. The polymer composition of claim 26 wherein said polymer is crosslinked by means of a multifunctional crosslinking co-monomer, said co-monomer being present in an amount from about 0.5–25% by weight, based upon total monomer weight.

28. The polymer composition of claim 27 wherein said crosslinking co-monomer is present in an amount from about 1–10% by weight, based upon total monomer weight.

29. The polymer composition of claim 26 wherein said monoreactive hydrophobic co-monomer is selected from the group consisting of styrene and fluorinated derivatives thereof; vinyl naphthalene and fluorinated derivatives thereof; ethyl vinylbenzene and fluorinated derivatives thereof; N-alkyl and N-aryl derivatives of acrylamide and methacrylamide, and fluorinated derivatives thereof; alkyl and aryl acrylates and fluorinated derivatives thereof; alkyl and aryl methacrylates and fluorinated derivatives thereof; 4-vinylbiphenyl and fluorinated derivatives thereof; 4-vinylanisole and fluorinated derivatives thereof; and 4-aminostyrene and fluorinated derivatives thereof.

30. The polymer composition of claim 26 wherein said polymer further comprises one or more amine co-monomers.

31. The polymer composition of claim 30 wherein said amine co-monomer is vinyl pyridine, dimethylaminomethyl styrene, or vinyl imidazole.

32. The polymer composition of claim 26 wherein said repeat unit (2) has the formula

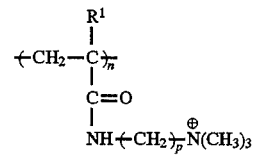

or copolymer thereof wherein $R^1$, n and p are as defined in claim 26.

33. The polymer composition of claim 32 wherein said monoreactive hydrophobic co-monomer is n-butylmethacrylamide, monoreactive hexafluorobutylmethacrylate, heptadecafluorodecylmethacrylate, styrene or a fluorinated derivative thereof, 2-vinyl naphthalene, 4-vinyl imidazole, vinyl pyridine, 4-vinylbiphenyl or a fluorinated derivative thereof, 4-vinylanisole or a fluorinated derivative thereof, or 4-aminostyrene or a fluorinated derivative thereof.

34. The polymer composition of claim 32 wherein said polymer further comprises a co-monomer selected from the group consisting of trimethylammoniumethylmethacrylate and trimethylammoniumethylacrylate.

35. The polymer composition of claim 26 wherein said repeat unit (2) has the formula

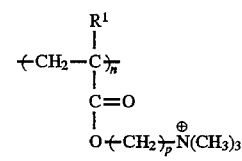

or copolymer thereof, wherein $R^1$, n and p are as defined in claim 26.

36. The polymer composition of claim 35 wherein said monoreactive hydrophobic co-monomer is isopropylacrylamide, styrene or a fluorinated derivative thereof or hexafluoroisopropylacrylate.

37. The polymer composition of claim 35 wherein said polymer further comprises, as a co-monomer, trimethylammoniumethylmethacrylate.

38. The polymer composition of claim 26 wherein said repeat unit (2) has the formula

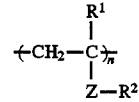

or copolymer thereof, wherein Z is $NR^3$ or $(CH_2)_m$, $R^2$ is

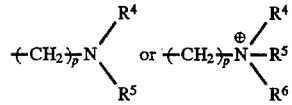

$R^1$, $R^3$, $R^4$, $R^5$, $R^6$, n, m and p are as defined in claim 26.

39. The polymer composition of claim 38 wherein said monoreactive hydrophobic co-monomer is selected from the group consisting of styrene and fluorinated derivatives thereof; vinyl naphthalene and fluorinated derivatives thereof; ethyl vinylbenzene and fluorinated derivatives thereof; N-alkyl and N-aryl derivatives of acrylamide and methacrylamide, and fluorinated derivatives thereof; alkyl and aryl acrylates and fluorinated derivatives thereof; alkyl and aryl methacrylates and fluorinated derivatives thereof; 4-vinylbiphenyl and fluorinated derivatives thereof;

4-vinylanisole and fluorinated derivatives thereof; and 4-aminostyrene and fluorinated derivatives thereof.

40. The polymer composition of claim 26 wherein said polymer further comprises one or more exchangeable counterions.

41. The polymer composition of claim 40 wherein at least one of said counterions is $Cl^-$, $Br^-$, $CH_3OSO_3^-$, $HSO_4^-$, $SO_4^{2-}$ $HCO_3^-$, $CO_3^{2-}$, acetate, lactate, succinate, propionate, butyrate, ascorbate, citrate, maleate, folate, an amino acid derivative, a nucleotide, a lipid, or a phospholipid.

42. A method for removing bile salts from a patient comprising administering to said patient a therapeutically effective amount of the reaction product of:

(a) one or more crosslinked polymers comprising a repeat unit having the formula:

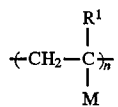

or copolymer thereof, where n is an integer; $R^1$ is H or a $C_1$–$C_8$ alkyl group; M is

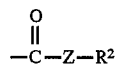

or —Z—$R^2$; Z is O, $NR^3$, S, or $(CH_2)_m$; m=0–10; $R^3$ is H or a $C_1$–$C_8$ alkyl group; and $R^2$ is

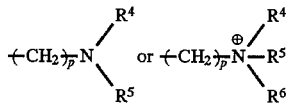

where p=0–10, and each $R^4$, $R^5$, and $R^6$, independently, is H, a $C_1$–$C_8$ alkyl group, or an aryl group; and (b) at least one alkylating agent, said reaction product being non-toxic and stable once ingested.

43. The method of claim 42 wherein said polymer is crosslinked by means of a multifunctional crosslinking co-monomer, said co-monomer being present in an amount from about 0.5–25% by weight, based upon total monomer weight.

44. The method of claim 43 wherein said crosslinking co-monomer is present in an amount from about 1–10% by weight, based upon total monomer weight.

45. The method of claim 42 wherein said repeat unit has the formula

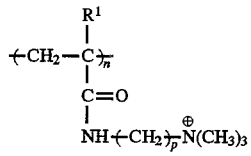

or copolymer thereof wherein $R^1$, n and p are as defined in claim 42.

46. The method of claim 42 wherein said repeat unit has the formula

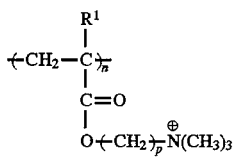

or copolymer thereof, wherein $R^1$, n and p are as defined in claim 42.

47. The method of claim 42 wherein said repeat unit has the formula

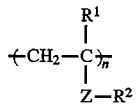

or copolymer thereof, wherein Z is $NR^3$ or $(CH_2)_m$, $R^2$ is

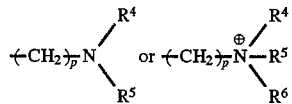

$R^1$, $R^3$, $R^4$, $R^5$, $R^6$, n, m and p are as defined in claim 42.

48. The method of claim 42 wherein said polymer further comprises one or more exchangeable counterions.

49. The method of claim 48 wherein at least one of said counterions is $Cl^-$, $Br^-$, $CH_3OSO_3^-$, $HSO_4^-$, $SO_4^{2-}$, $HCO_3^-$, $CO_3^{2-}$, acetate, lactate, succinate, propionate, butyrate, ascorbate, citrate, maleate, folate, an amino acid derivative, a nucleotide, a lipid, or a phospholipid.

50. The method of claim 42 wherein said alkylating agent has the formula RX where R is a $C_1$–$C_{20}$ alkyl, $C_1$–$C_{20}$ hydroxyalkyl, $C_1$–$C_{20}$ aralkyl, $C_1$–$C_{20}$ alkylammonium, or $C_1$–$C_{20}$ alkylamido group and X is one or more electrophilic leaving groups.

51. The method of claim 50 wherein X is a halide, epoxy, tosylate, or mesylate group.

52. The method of claim 51 wherein said alkylating agent is a $C_1$–$C_{20}$ alkyl halide.

53. The method of claim 51 wherein said alkylating agent is a $C_1$–$C_{20}$ alkyl halide ammonium salt.

54. The method of claim 51 wherein said alkylating agent is a $C_1$–$C_{20}$ dihaloalkane, $C_1$–$C_{20}$ hydroxyalkyl halide, $C_1$–$C_{20}$ aralkyl halide, $C_1$–$C_{20}$ alkyl epoxy ammonium salt, a $C_1$–$C_{20}$ epoxy alkylamide.

55. The method of claim 42 wherein said polymer is reacted with at least two alkylating agents, one of said alkylating agents having the formula RX where R is a $C_4$–$C_{20}$ alkyl group and X is one or more electrophilic leaving groups, and the other of said alkylating agents having the formula R'X where R' is a $C_1$–$C_{20}$ alkyl ammonium group and X is one or more electrophilic leaving groups.

56. The method of claim 42 wherein said polymer is reacted with at least two alkylating agents, one of said alkylating agents having the formula RX where R is a $C_1$–$C_{20}$ alkyl group and X is one or more electrophilic leaving groups, and the other of said alkylating agents having the formula R'X where R' is a $C_1$–$C_{20}$ hydroxyalkyl group and X is one or more electrophilic leaving groups.

57. The method of claim 42 wherein said polymer is reacted with at least two alkylating agents, one of said alkylating agents is a $C_1$–$C_{20}$ dihaloalkane and the other of said alkylating agents is a $C_1$–$C_{20}$ alkylammonium salt.

58. A therapeutic composition effective for removing bile salts by ion exchange comprising a therapeutic amount of the reaction product of:

(a) one or more crosslinked polymers comprising a repeat unit having the formula:

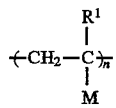

or copolymer thereof, where n is an integer; $R^1$ is H or a $C_1$-$C_s$ alkyl group; M is

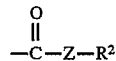

or —Z—$R^2$; Z is O, $NR^3$, S, or $(CH_2)_m$; m=0–10; $R^1$ is H or a $C_1$-$C_8$ alkyl group; and $R^2$ is

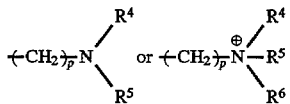

where p=0–10, and each $R^4$, $R^5$, and $R^6$, independently, is H, a $C_1$-$C_8$ alkyl group, or an aryl group; and (b) at least one alkylating agent in a pharmaceutically acceptable carrier, said reaction product being non-toxic and stable once ingested.

59. A polymer composition effective for removing bile salts by ion exchange comprising a therapeutic amount of the reaction product of:

(a) one or more crosslinked polymers comprising a repeat unit having the formula:

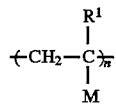

or copolymer thereof, where n is an integer; $R^1$ is H or a $C_1$-$C_8$ alkyl group; M is —C—Z—$R^2$ or —Z—$R^2$; Z is O, $NR^3$, S, or $(CH_2)_m$; m=0–10; $R^3$ is H or a $C_1$-$C_8$ alkyl group; and $R^2$ is

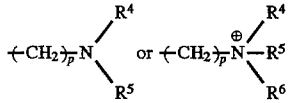

where p - 0–10, and each $R^4$, $R^5$, and $R^6$, independently, is H, a $C_1$-$C_8$ alkyl group, or an aryl group; and (b) at least one alkylating agent, said reaction product being non-toxic and stable once ingested.

60. The polymer composition of claim 59 wherein said polymer is crosslinked by means of a multifunctional crosslinking co-monomer, said co-monomer being present in an amount from about 0.5–25% by weight, based upon total monomer weight.

61. The polymer composition of claim 60 wherein said crosslinking co-monomer is present in an amount from about 1–10% by weight, based upon total monomer weight.

62. The polymer composition of claim 59 wherein said repeat unit has the formula

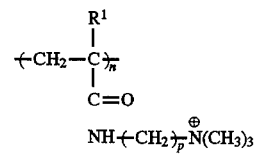

or copolymer thereof wherein $R^1$, n and p are as defined in claim 59.

63. The polymer composition of claim 59 wherein said repeat unit has the formula

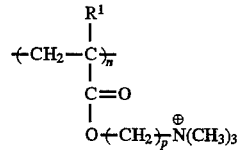

or copolymer thereof, wherein $R^1$, n and p are as defined in claim 59.

64. The polymer composition of claim 59 wherein said repeat unit has the formula

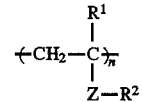

or copolymer thereof, wherein Z is $NR^3$ or $(CH_2)_m$, $R^2$ is

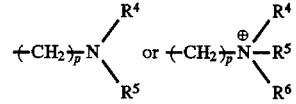

$R^1$, $R^3$, $R^4$, $R^5$, $R^6$, n, m and p are as defined in claim 59.

65. The polymer composition of claim 59 wherein said polymer further comprises one or more exchangeable counterions.

66. The polymer composition of claim 65 wherein at least one of said counterions is $Cl^-$, $Br^-$, $CH_3OSO_3^-$, $HSO_4^-$, $SO_4^{2-}$, $HCO_3^-$, $CO_3^{2-}$, acetate, lactate, succinate, propionate, butyrate, ascorbate, citrate, maleate, folate, an amino acid derivative, a nucleotide, a lipid, or a phospholipid.

67. The polymer composition of claim 59 wherein said alkylating agent has the formula Rx where R is a $C_1$-$C_{20}$ alkyl, $C_1$-$C_{20}$ hydroxyalkyl, $C_1$-$C_{20}$ aralkyl, $C_1$-$C_{20}$ alkylammonium, or $C_1$-$C_{20}$ alkylamido group and X is one or more electrophilic leaving groups.

68. The polymer composition of claim 67 wherein X is a halide, epoxy, tosylate, or mesylate group.

69. The polymer composition of claim 68 wherein said alkylating agent is a $C_4$-$C_{20}$ alkyl halide.

70. The polymer composition of claim 68 wherein said alkylating agent is a $C_1$-$C_{20}$ alkyl halide ammonium salt.

71. The polymer composition of claim 68 wherein said alkylating agent is a $C_1$-$C_{20}$ dihaloalkane, $C_1$-$C_{20}$ hydroxyalkyl halide, $C_1$-$C_{20}$ aralkyl halide, $C_1$-$C_{20}$ alkyl epoxy ammonium salt, a $C_1$-$C_{20}$ epoxy alkylamide.

72. The polymer composition of claim 59 wherein said polymer is reacted with at least two alkylating agents, one of said alkylating agents having the formula RX where R is a $C_4$-$C_{20}$ alkyl group and X is one or more electrophilic leaving groups, and the other of said alkylating agents having the formula R'X where R' is a $C_1$-$C_{20}$ alkyl ammonium group and X is one or more electrophilic leaving groups.

73. The polymer composition of claim 59 wherein said polymer is reacted with at least two alkylating agents, one of said alkylating agents having the formula RX where R is a $C_1$–$C_{20}$ alkyl group and X is one or more electrophilic leaving groups, and the other of said alkylating agents having the formula R'X where R' is a $C_1$–$C_{20}$ hydroxyalkyl group and X is one or more electrophilic leaving groups.

74. The polymer composition of claim 59 wherein said polymer is reacted with at least two alkylating agents, one of said alkylating agents is a $C_1$–$C_{20}$ dihaloalkane and the other of said alkylating agents is a $C_1$–$C_{20}$ alkylammonium salt.

* * * * *

UNITED STATES PATENT AND TRADEMARK OFFICE
CERTIFICATE OF CORRECTION

PATENT NO. : 5,624,963
DATED : April 29, 1997
INVENTOR(S) : W. Harry Mandeville, III and Stephen Randall Holmes-Farley It is certified that error appears in the above-indentified patent and that said Letters Patent is hereby corrected as shown below:

In Column 24, next to last line:   After "NR$^3$" and before "S", insert --,--;

In Column 25, line 60:   Delete "Claim 11" and insert therefor --Claim 1--; and

In Column 25, line 65:   Delete "Claim 11" and insert therefor --Claim 1--.

Signed and Sealed this

Seventh Day of October, 1997

Attest:

BRUCE LEHMAN

Attesting Officer    Commissioner of Patents and Trademarks